United States Patent
Blanchard et al.

(10) Patent No.: US 12,403,284 B2
(45) Date of Patent: Sep. 2, 2025

(54) CATHETER ASSEMBLY WITH ANGLE CHANGING AND RELATED METHODS

(71) Applicant: Becton, Dickinson and Company, Franklin Lakes, NJ (US)

(72) Inventors: Curtis H. Blanchard, Riverton, UT (US); Megan Scherich, Salt Lake City, UT (US); Weston F. Harding, Lehi, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 605 days.

(21) Appl. No.: 17/474,545

(22) Filed: Sep. 14, 2021

(65) Prior Publication Data
US 2022/0080153 A1 Mar. 17, 2022

Related U.S. Application Data

(60) Provisional application No. 63/078,638, filed on Sep. 15, 2020.

(51) Int. Cl.
*A61M 25/00* (2006.01)
*A61M 39/10* (2006.01)

(52) U.S. Cl.
CPC ........ *A61M 25/0097* (2013.01); *A61M 39/10* (2013.01); *A61M 2039/1077* (2013.01)

(58) Field of Classification Search
CPC .............. A61M 25/0097; A61M 39/10; A61M 2039/1077
See application file for complete search history.

(56) References Cited

U.S. PATENT DOCUMENTS

| | | | | |
|---|---|---|---|---|
| 1,332,598 A | * | 3/1920 | Boyd | B61K 5/00 254/93 H |
| 2,136,770 A | * | 11/1938 | Witzenmann | F16L 11/18 138/120 |

(Continued)

FOREIGN PATENT DOCUMENTS

| | | | |
|---|---|---|---|
| AU | 2019204458 A1 * | 7/2019 | ........ A61M 25/0014 |
| CN | 110339458 | * 10/2019 | |

(Continued)

OTHER PUBLICATIONS

Speed News, 'How to Measure Camshaft Lift'. Dec. 27, 2019 [Database online] [Retrieved on Dec. 14, 2024] Retrieved from The Way Back Machine, https://web.archive.org/web/20191227190533/ https://nasaspeed.news/toolshed-engineer/how-to-measure-camshaft-lift/ (Year: 2019).*

*Primary Examiner* — Nathan R Price
*Assistant Examiner* — Mark A Igel
(74) *Attorney, Agent, or Firm* — The Webb Law Firm

(57) ABSTRACT

A catheter assembly may include a catheter adapter, which may include a distal end, a proximal end, and a lumen extending through the distal end and the proximal end. The catheter assembly may include a catheter secured within the catheter adapter and extending from the distal end of the catheter adapter. The catheter adapter may be configured to move between a first position and a second position. In response to the catheter adapter moving from the first position to the second position, an angle of the catheter adapter with respect to an insertion surface may be configured to increase, which may improve patency of the catheter assembly and alignment of a fluid path of the catheter assembly with vasculature of a patient.

15 Claims, 18 Drawing Sheets

(56) References Cited

U.S. PATENT DOCUMENTS

| | | | | |
|---|---|---|---|---|
| 2,409,432 | A * | 10/1946 | Hubbard | A61M 25/02 604/179 |
| 4,212,297 | A * | 7/1980 | Frosch | A61M 16/0465 128/207.14 |
| 4,601,701 | A * | 7/1986 | Mueller, Jr. | A61M 25/00 D24/129 |
| 4,733,661 | A * | 3/1988 | Palestrant | A61B 17/3403 604/116 |
| 4,874,378 | A * | 10/1989 | Hillstead | A61M 25/0662 604/533 |
| 5,020,933 | A * | 6/1991 | Salvestro | F16M 11/2078 403/90 |
| 5,368,592 | A * | 11/1994 | Stern | A61M 25/0147 604/95.05 |
| 5,916,194 | A * | 6/1999 | Jacobsen | A61M 25/0105 604/524 |
| 5,941,653 | A * | 8/1999 | Cipriani | B60M 1/20 403/373 |
| 5,941,889 | A * | 8/1999 | Cermak | A61B 8/0841 606/130 |
| 6,361,499 | B1 * | 3/2002 | Bates | A61B 17/3403 600/464 |
| 9,033,880 | B2 * | 5/2015 | Sheldon | A61B 8/4455 600/437 |
| 10,143,810 | B2 * | 12/2018 | Saeed Malik | A61M 5/427 |
| 2009/0149814 | A1 * | 6/2009 | Bailey | A61M 25/02 604/180 |
| 2010/0042111 | A1 * | 2/2010 | Qureshi | F16M 11/14 606/130 |
| 2012/0123343 | A1 * | 5/2012 | Aviles | A61M 25/02 604/174 |
| 2012/0215173 | A1 * | 8/2012 | Wright | A61M 5/158 604/174 |
| 2014/0142538 | A1 * | 5/2014 | Hyman | A61F 13/05 604/500 |
| 2015/0038909 | A1 * | 2/2015 | Christensen | A61M 25/0625 604/164.07 |
| 2016/0022454 | A1 * | 1/2016 | Bonutti | A61M 25/065 623/1.12 |
| 2017/0239443 | A1 | 8/2017 | Abitabilo et al. | |
| 2017/0368308 | A1 * | 12/2017 | Hofius | A61M 25/0097 |
| 2020/0246592 | A1 * | 8/2020 | Clavijo | A61M 25/0097 |
| 2020/0360668 | A1 * | 11/2020 | Blanchard | A61M 39/22 |
| 2020/0376234 | A1 * | 12/2020 | Cheng | A61M 25/0097 |

FOREIGN PATENT DOCUMENTS

| | | | |
|---|---|---|---|
| CN | 110339458 A | 10/2019 | |
| DE | 102018106198 A1 * | 5/2019 | ......... A61B 10/0233 |
| EP | 0023580 B1 | 2/1985 | |
| WO | WO-9515192 A1 * | 6/1995 | .......... A61M 1/3653 |

\* cited by examiner

CATHETER ASSEMBLY WITH ANGLE CHANGING AND RELATED METHODS

The present application claims priority to U.S. Application Ser. No. 63/078,638, entitled "Catheter Assembly With Angle Changing and Related Methods" filed Sep. 15, 2020, the entire disclosure of which is hereby incorporated by reference intis entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and the introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may remove the needle, leaving the catheter in place for future blood withdrawal or fluid infusion.

Blood withdrawal using the catheter may be difficult for several reasons, particularly when a dwell time of the catheter within the vasculature is more than one day. When the catheter is left inserted in the patient for a prolonged period of time, the catheter or vein may be more susceptible to narrowing, collapse, kinking, blockage by debris (e.g., fibrin or platelet clots), and adhering of a tip of the catheter to the vasculature. Due to this, the catheter may become compromised for infusion, blood draw, or aspiration over time. The catheter is often used for acquiring a blood sample at a time of catheter placement, but the catheter is less frequently used for acquiring a blood sample during the catheter dwell period. Therefore, when a blood sample is required, an additional needle stick is often used to provide vein access for blood collection, which may be painful for the patient and result in higher material costs.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access systems and related devices and methods. In some embodiments, a catheter assembly may be configured to provide angle changing of a catheter, which may reduce a likelihood of occlusion of the catheter, improve patency, and facilitate alignment of a fluid path of the catheter assembly with vasculature of a patient.

In some embodiments, the catheter assembly may include a catheter adapter, which may include a distal end, a proximal end, and a lumen extending through the distal end of the catheter adapter and the proximal end of the catheter adapter. In some embodiments, the catheter assembly may include the catheter secured within the catheter adapter and extending from the distal end of the catheter adapter.

In some embodiments, the catheter assembly may include an expandable support coupled to the catheter adapter. In some embodiments, the expandable support may be configured to adjust an angle of the catheter adapter with respect to skin of the patient. In some embodiments, the expandable support may be configured to move from a diminished position to an expanded position in response to an infusion of liquid or air into the expandable support. In some embodiments, in response to the expandable support being moved from the diminished position to the expanded position, an angle of the catheter adapter with respect to an insertion surface may be configured to increase.

In some embodiments, the expandable support may include a telescoping member. In some embodiments, the expandable support may be configured to move from the diminished position to the expanded position in response to extension of the telescoping member. In some embodiments, in response to the expandable support being moved from the diminished position to the expanded position, an angle of the catheter adapter with respect to an insertion surface may be configured to increase.

In some embodiments, a protrusion may be coupled to the catheter adapter. In some embodiments, the protrusion may be configured to rotate. In some embodiments, in response to the protrusion being rotated from a first position to a second position, an angle of the catheter adapter with respect to an insertion surface may be configured to increase. In some embodiments, in response to the protrusion being rotated from the first position to the second position, the catheter adapter rotates with the protrusion.

In some embodiments, the catheter assembly may include a platform. In some embodiments, in response to the protrusion being in the first position, the catheter adapter may rest on the platform. In some embodiments, in response to the protrusion being rotated to the second position, the protrusion may rest on the platform, and the catheter adapter may be spaced apart from the platform. In these and other embodiments, the catheter adapter and the protrusion may be monolithically formed as a single unit.

In some embodiments, the catheter assembly may include a strap disposed over the catheter adapter and the protrusion. In some embodiments, a first end and a second end of the strap may be coupled to the platform. In some embodiments, at least a portion of the strap may be elastomeric. In some embodiments, the catheter assembly may include another strap disposed over the catheter adapter and the protrusion. In some embodiments, a first end and a second end of the other strap may be coupled to the platform. In some embodiments, at least a portion of the other strap may be elastomeric. In some embodiments, the catheter adapter may include a side port disposed between the distal end of the catheter adapter and the proximal end of the catheter adapter. In some embodiments, the side port may be disposed between the strap and the other strap.

In some embodiments, the catheter assembly may include a collar that rotates with respect to the catheter adapter. In some embodiments, the collar may include the protrusion. In some embodiments, the collar may be asymmetric.

In some embodiments, the catheter adapter may be configured to move between a particular first position and a particular second position. In some embodiments, in response to the catheter adapter moving from the particular first position to the particular second position, an angle of the catheter adapter with respect to an insertion surface may be configured to increase.

In some embodiments, the catheter assembly may include a platform that is pivotally coupled to the catheter adapter. In some embodiments, the catheter adapter may be configured to pivot between the particular first position and the particular second position or any number of positions in between the first position and the second position. In some embodiments, in response to the catheter adapter pivoting from the particular first position to the particular second position, an angle of the catheter adapter with respect to the insertion surface is configured to increase.

In some embodiments, the catheter assembly may include a platform coupled to the catheter adapter. In some embodiments, the platform may include a first planar surface and a second planar surface proximate the first planar surface. In some embodiments, the first planar surface may be angled with respect to the second planar surface. In some embodiments, the catheter adapter is configured to rock between the particular first position to the particular second position. In some embodiments, in response to the catheter adapter rocking from the particular first position to the particular second position, the angle of the catheter adapter with respect to the insertion surface is configured to increase.

In some embodiments, the catheter adapter may include a slot. In some embodiments, the catheter assembly may include a slider extending through the slot and configured to move between a proximal position and a distal position. In some embodiments, in response to the slider moving from the proximal position to the distal position, the slider may push on the distal end of the catheter adapter to increase the angle of the catheter adapter with respect to the insertion surface.

In some embodiments, the catheter adapter may include a wing and a wall extending generally perpendicular to the wing. In some embodiments, the slot is disposed within the wall. In some embodiments, the slider may be arched. In some embodiments, the slider may include a push tab.

In some embodiments, the catheter assembly may include a catheter adjuster, which may include a distal end, a proximal end, and the catheter extending there through. In some embodiments, the catheter adjuster may be coupled to the distal end of the catheter adapter at a ball joint or a hinge. In some embodiments, in response to the catheter adjuster moving from another particular first position to another particular second position via the ball joint or the hinge, an angle of the catheter with respect to an insertion surface may be configured to increase. In some embodiments, the catheter assembly may include a collar disposed around the distal end of the catheter adapter. In some embodiments, the collar may be configured to lock the ball joint in the other particular first position or the other particular second position or any number of positions in between the other particular first position and the other particular second position.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which.

DETAILED DESCRIPTION

Figure 1A:
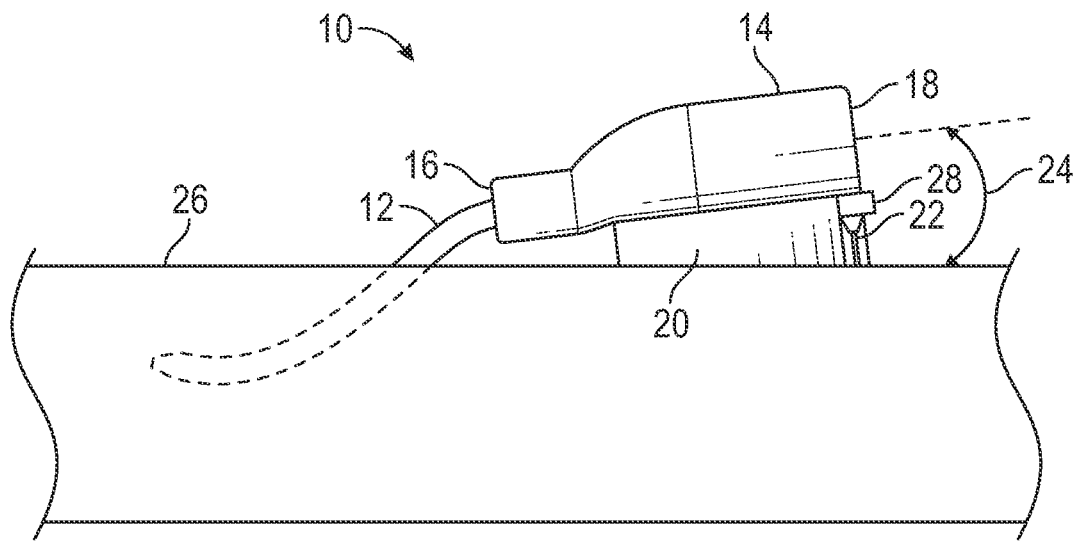
FIG. 1A is an upper perspective view of an example catheter assembly, illustrating an example expandable support in an example diminished position, according to some embodiments.

Referring now to FIGS. 1A-1L, in some embodiments, a catheter assembly 10 may be configured to provide angle changing of a catheter 12, which may reduce a likelihood of occlusion of the catheter 12, improve patency, and facilitate alignment of a fluid path of the catheter assembly 10 with vasculature of a patient. In some embodiments, the catheter assembly 10 may also move the catheter 12 radially, distally and/or proximally within the vasculature, which may also reduce the likelihood of occlusion and improve patency. In some embodiments, the angle changing provided by the catheter assembly 10 may facilitate blood draw, fluid delivery, patient or device monitoring, or other clinical needs.

In some embodiments, the catheter assembly 10 may include a catheter adapter 14, which may include a distal end 16, a proximal end 18, and a lumen extending through the distal end 16 and the proximal end 18. In some embodiments, the catheter assembly 10 may include the catheter 12 secured within the catheter adapter 14 and extending from the distal end 16 of the catheter adapter 14.

In some embodiments, the catheter assembly 10 may include an expandable support 20 coupled to the catheter adapter 14. In some embodiments, the expandable support 20 may be configured to adjust an angle of the catheter adapter 14 with respect to skin of the patient.

Figure 1B:
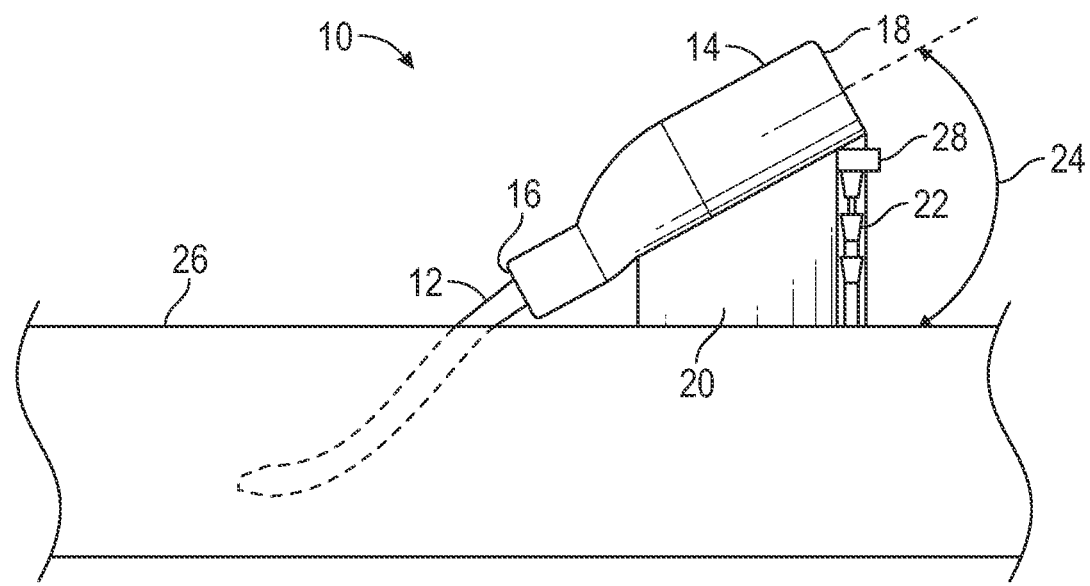
FIG. 1B is an upper perspective view of the catheter assembly of FIG. 1A, illustrating the expandable support in an example expanded position, according to some embodiments.

In some embodiments, the expandable support 20 may include a telescoping member 22, as illustrated, for example, in FIGS. 1A-1B, or another suitable mechanical device to change a height of the proximal end 18 of the catheter adapter 14. In some embodiments, the expandable support 20 may be configured to move from a diminished position, illustrated, for example, in FIG. 1A, to an expanded position, illustrated, for example, in FIG. 1B in response to extension of the telescoping member 22. In some embodiments, the telescoping member 22 may be configured to lock in a particular position.

In some embodiments, in response to the expandable support 20 being moved from the diminished position to the expanded position, an angle 24 of the catheter adapter 14 with respect to an insertion surface 26 may be configured to increase. In some embodiments, the angle 24 may be measured between a central axis of the catheter adapter and the insertion surface 26. In these embodiments, the proximal end 18 of the catheter adapter 14 may be lifted up, which may alter a position of the catheter 12. In some embodiments, as illustrated, in FIGS. 1A-1B, the insertion surface 26 may include skin of the patient.

In some embodiments, a tab 28 may be coupled to the telescoping member 22. In some embodiments, a user may grip the tab 28 and move the expandable support 20 from the diminished position to the expanded position. In some embodiments, the expandable support 20 may be configured to move from the diminished position to the expanded position in response to an infusion of liquid or air into the expandable support 20.

Figure 1C:
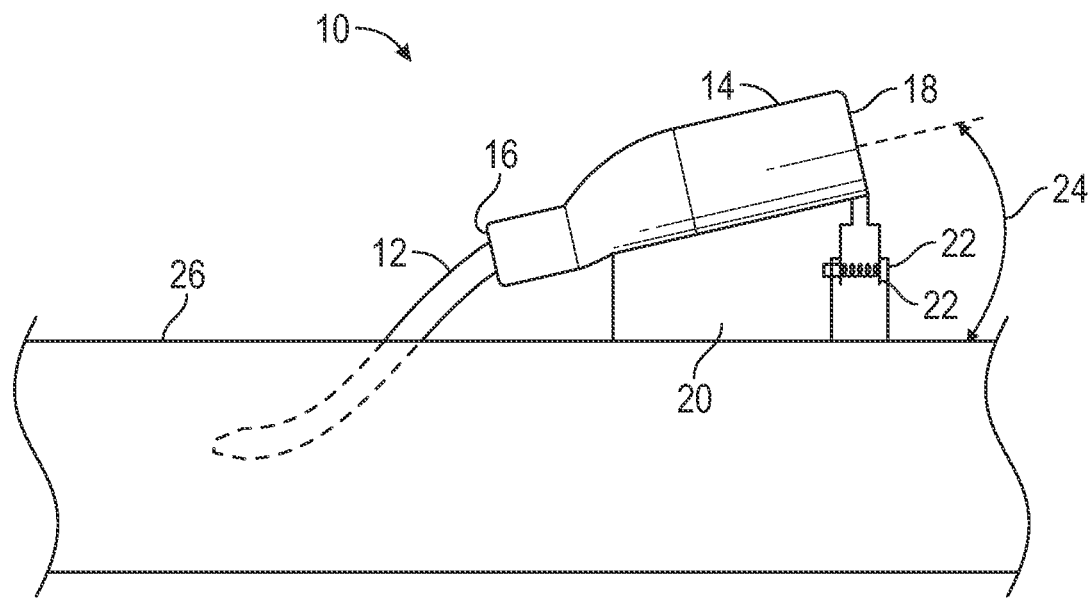
FIG. 1C is an upper perspective view of the catheter assembly of FIG. 1A, illustrating an example spring-loaded locking mechanism and the expandable support in the expanded position, according to some embodiments.
Figure 1D:
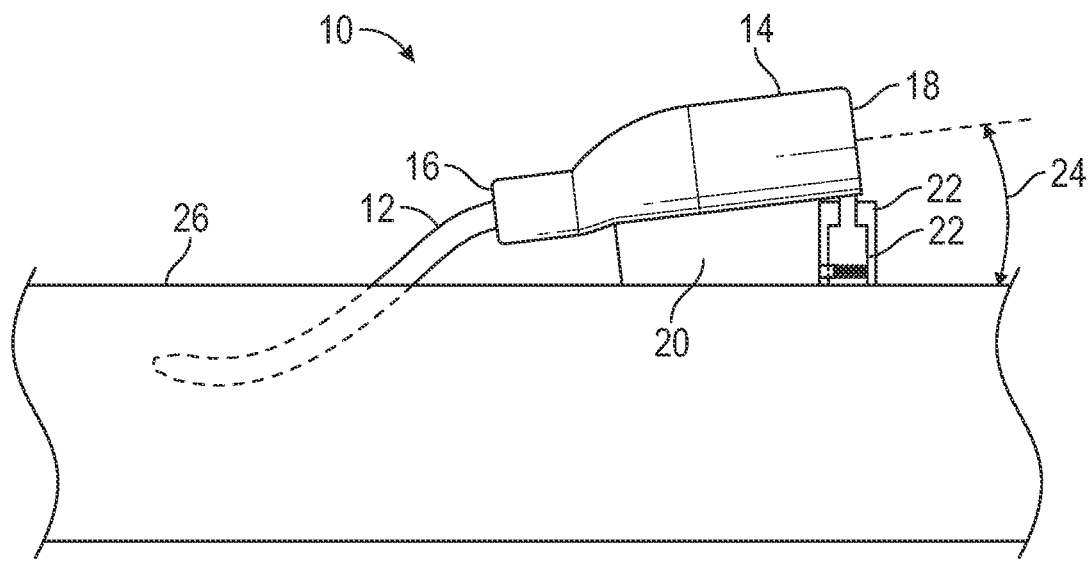
FIG. 1D is an upper perspective view of the catheter assembly of FIG. 1A, illustrating the spring-loaded locking mechanism and the expandable support in the diminished position, according to some embodiments.

As illustrated in FIGS. 1C-1D, in some embodiments, the telescoping member 22 may be coupled to a spring-loaded locking mechanism. In some embodiments, the spring-loaded locking mechanism may include a spring coupled to a button and the telescoping member 22. In some embodiments, in response to raising or lengthening the telescoping member 22, the button may extend through a hole in the telescoping member 22 to secure to the telescoping member in an extended position.

Figure 1E:
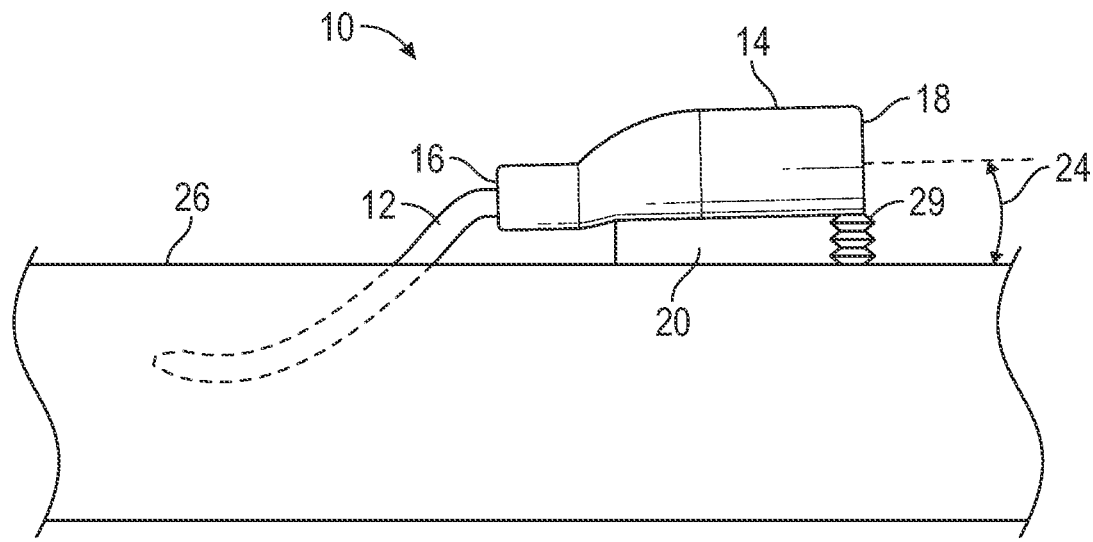
FIG. 1E is an upper perspective view of the catheter assembly of FIG. 1A, illustrating an example accordion and the expandable support in the diminished position, according to some embodiments.
Figure 1F:
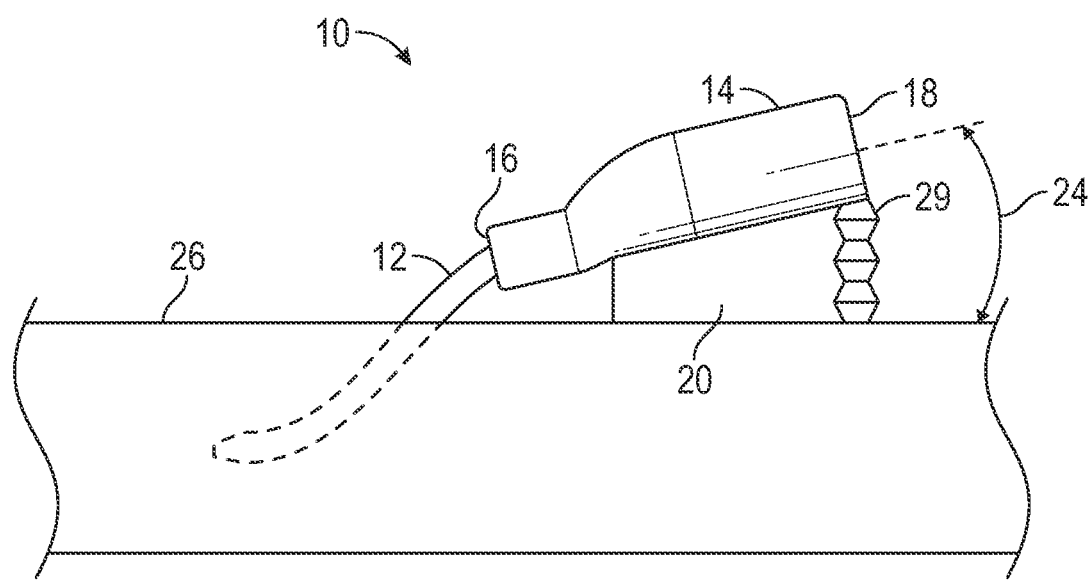
FIG. 1F is an upper perspective view of the catheter assembly of FIG. 1A, illustrating an example accordion and the expandable support in the expanded position, according to some embodiments.

As illustrated in FIGS. 1E-1F, the expandable support 20 may include another suitable mechanical device, such as an accordion extension 29, to change the height of the proximal end 18 of the catheter adapter 14. In some embodiments, the expandable support 20 may be configured to move from the diminished position, illustrated, for example, in FIG. 1E, to the expanded position, illustrated, for example, in FIG. 1F in response to expansion of the accordion extension 29. In some embodiments, in response to the accordion extension 29 being in the expanded position, the accordion extension 29 may be configured to remain in the expanded position until additional force from the user. In some embodiments, the accordion extension 29 may be constructed of plastic or another suitable material.

Figure 1G:
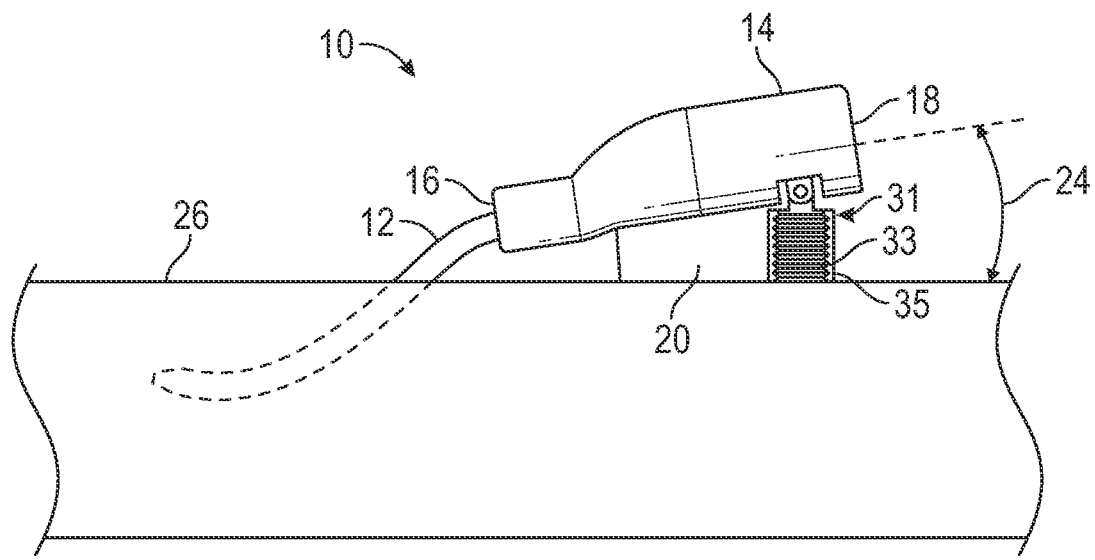
FIG. 1G is an upper perspective view of the catheter assembly of FIG. 1A, illustrating an example threaded extension and the expandable support in the diminished position, according to some embodiments.
Figure 1H:
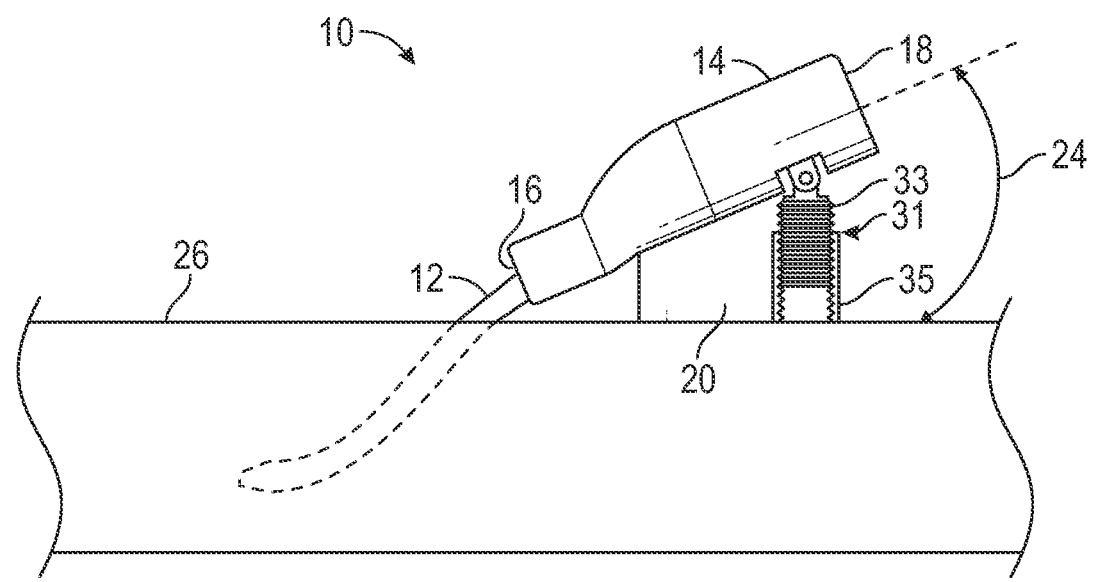
FIG. 1H is an upper perspective view of the catheter assembly of FIG. 1A, illustrating the threaded extension and the expandable support in the expanded position, according to some embodiments.

As illustrated in FIGS. 1G-1H, the expandable support 20 may include another suitable mechanical device, such as a threaded extension 31, to change the height of the proximal end 18 of the catheter adapter 14. In some embodiments, the threaded extension 31 may be configured to move from the diminished position, illustrated, for example, in FIG. 1G, to the expanded position, illustrated, for example, in FIG. 1H in response to unthreading of an upper portion 33 of the threaded extension 31 with respect to a lower portion 35 of the threaded extension of the accordion extension 29. In some embodiments, the upper portion 33 may include external threads, and the lower portion 35 may include internal threads. In some embodiments, the catheter adapter 14 may rotate with respect to the upper portion 33.

Figure 1I:
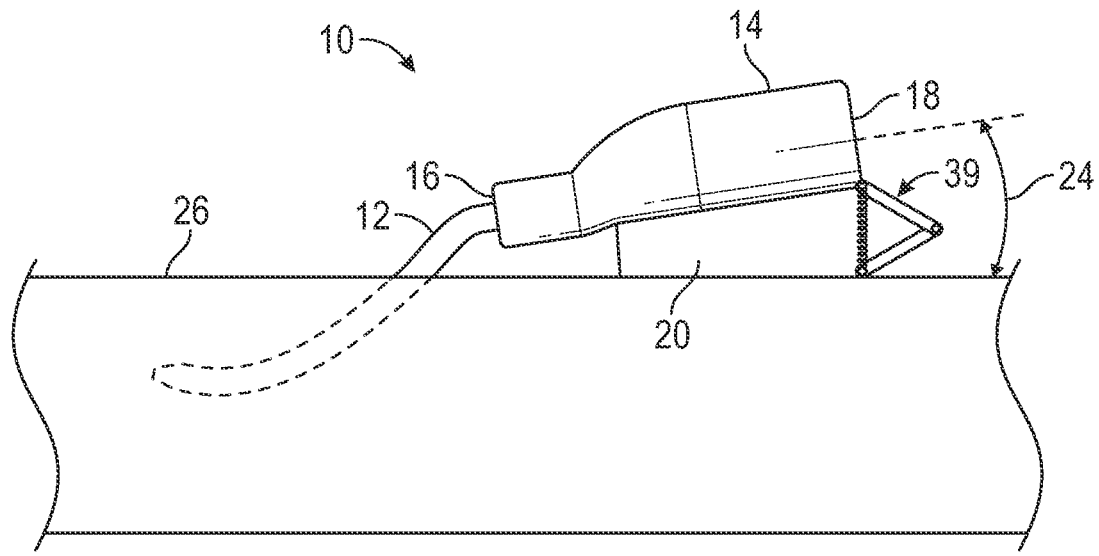
FIG. 1I is an upper perspective view of the catheter assembly of FIG. 1A, illustrating an example hinge and the expandable support in the diminished position, according to some embodiments.
Figure 1J:
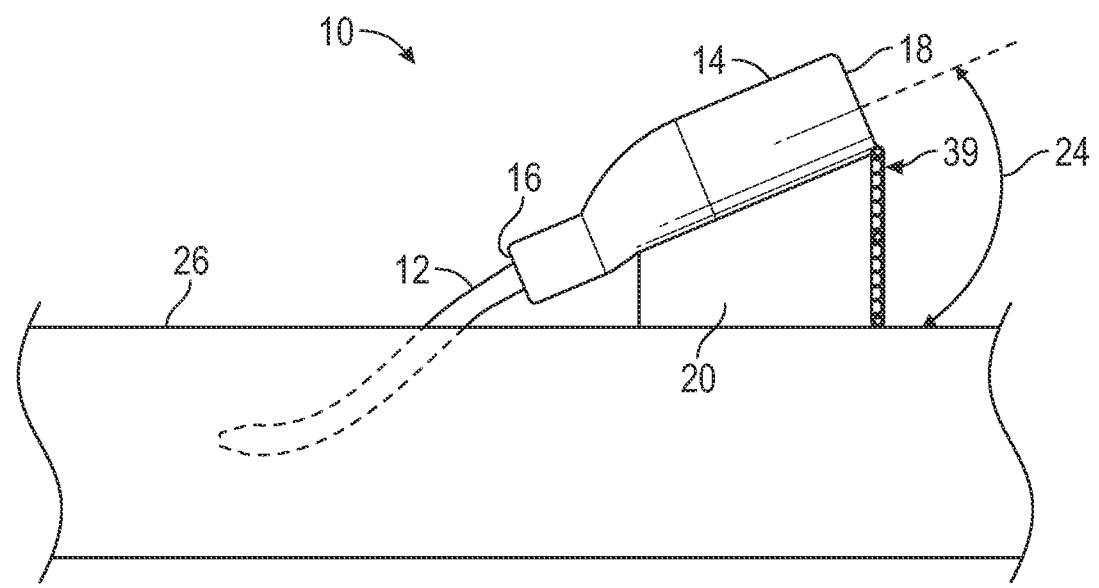
FIG. 1J is an upper perspective view of the catheter assembly of FIG. 1A, illustrating the hinge and the expandable support in the expanded position, according to some embodiments.

As illustrated in FIGS. 1I-1J, the expandable support 20 may include another suitable mechanical device, such as a hinge 39, to change the height of the proximal end 18 of the catheter adapter 14. In some embodiments, the expandable support 20 may be configured to move from the diminished position, illustrated, for example, in FIG. 1I, to the expanded position, illustrated, for example, in FIG. 1J in response to expansion of the hinge 39. In some embodiments, a spring may extend between ends of the hinge 39 to provide support.

Figure 1K:
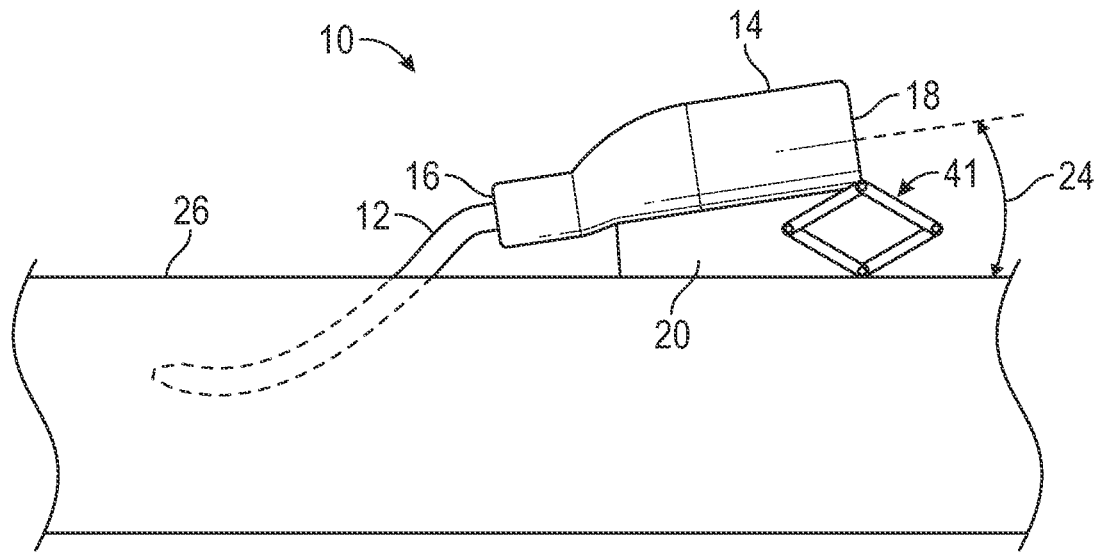
FIG. 1K is an upper perspective view of the catheter assembly of FIG. 1A, illustrating an example multi-hinge extender and the expandable support in the diminished position, according to some embodiments.
Figure 1L:
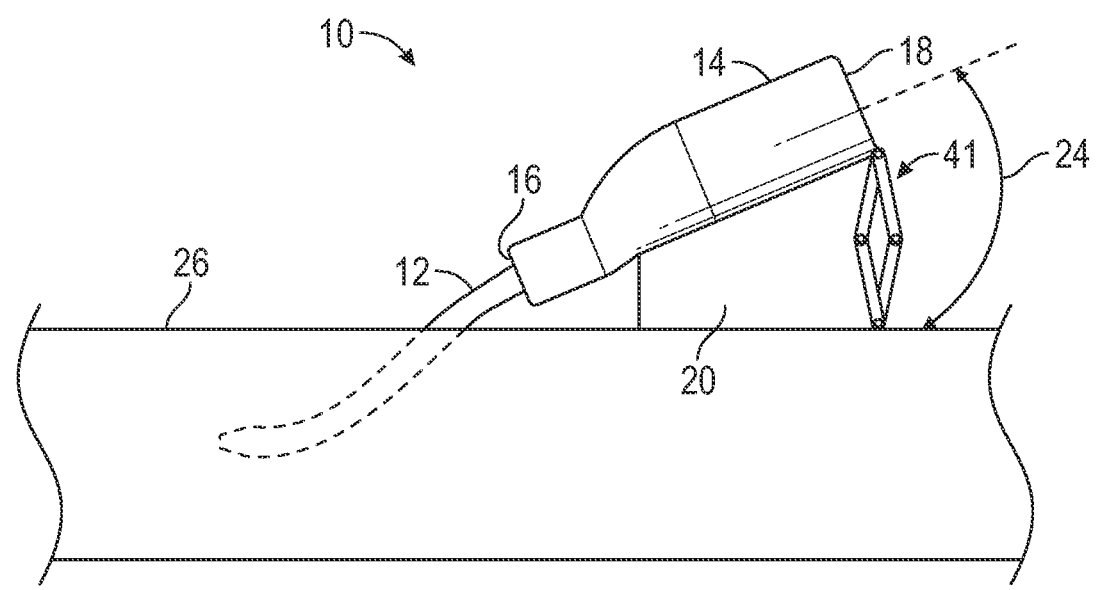
FIG. 1L is an upper perspective view of the catheter assembly of FIG. 1A, illustrating the multi-hinge extender and the expandable support in the expanded position, according to some embodiments.

As illustrated in FIGS. 1K-1L, the expandable support 20 may include another suitable mechanical device, such as a multi-hinge extender 41, to change the height of the proximal end 18 of the catheter adapter 14. In some embodiments, the expandable support 20 may be configured to move from the diminished position, illustrated, for example, in FIG. 1K, to the expanded position, illustrated, for example, in FIG. 1K in response to opposing hinges of the multi-hinge extender 41 moving closer to each other. In some embodiments, the multi-hinge extender 41 may include the opposing hinges and another pair of opposing hinges, and may form a diamond shape.

Figure 1M:
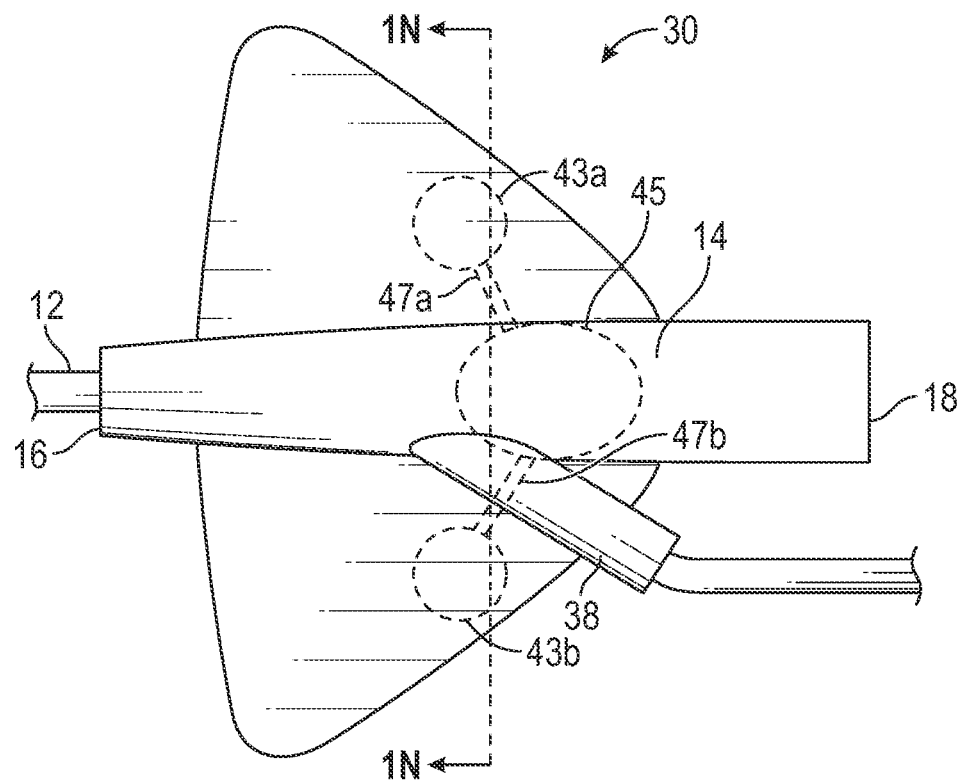
FIG. 1M is an upper perspective view of another catheter assembly, illustrating an example expandable pocket and example compressible pockets, according to some embodiments.
Figure 1N:
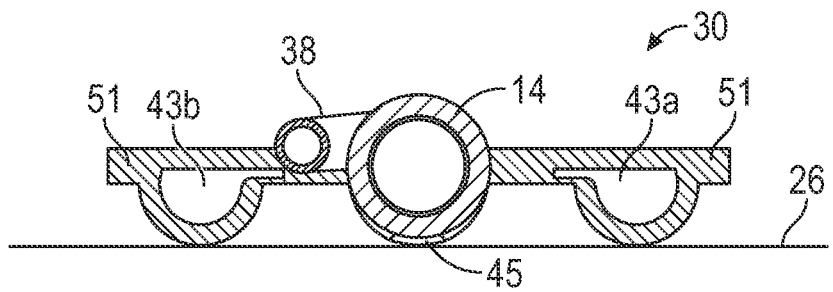
FIG. 1N is an upper perspective view of the catheter assembly of FIG. 1M, illustrating the compressible pockets filled with liquid or gas, according to some embodiments.
Figure 1O:
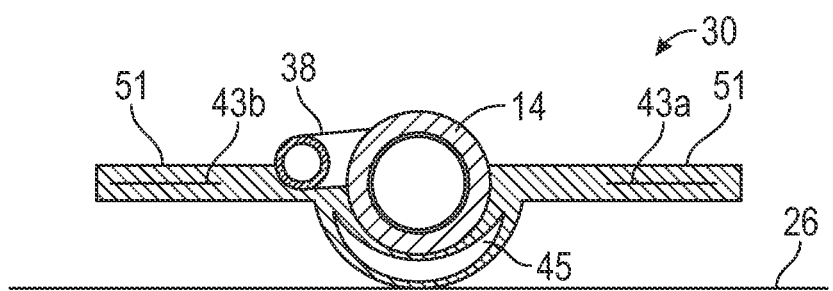
FIG. 1O is an upper perspective view of the catheter assembly of FIG. 1M, illustrating the expandable pocket filled with liquid or gas, according to some embodiments.

Referring now to FIGS. 1M-1O, in some embodiments, the catheter assembly 10 may include one or more compressible pockets 43 and/or an expandable pocket 45 to provide angle changing of the catheter 12 and/or positioning of the catheter 12 within the vasculature. In some embodiments, the compressible pockets 43 may be filled with liquid or gas and connected to the expandable pocket via channels 47. In some embodiments, in response to compression of the compressible pockets 43, the liquid or the gas may flow from the compressible pockets 43, through the channels 47, and into the expandable pocket 45, which may expand to change the angle of the catheter 12. In some embodiments, the expandable pocket 45 may be disposed beneath the catheter adapter and/or coupled to the catheter adapter 14 or a platform beneath the catheter adapter 14. In some embodiments, the expandable pocket 45 may be centrally located between skin of the patient and the catheter adapter 14. In some embodiments, the compressible pockets 43 may be disposed within one or more wings 51 extending outwardly from the catheter adapter 14. In some embodiments, there may be a particular compressible pocket 43 within each of the wings 51, on opposing sides of the catheter adapter 14 for balance.

In some embodiments, in response to a desire to reduce a curve of the catheter 12 to reduce kinking for infusion or blood draw or when there is an occlusion, the user may press on the wings 51 and compress the compressible pockets 43 to inflate the expandable pocket 45 and raise the catheter adapter 14.

Figure 1P:
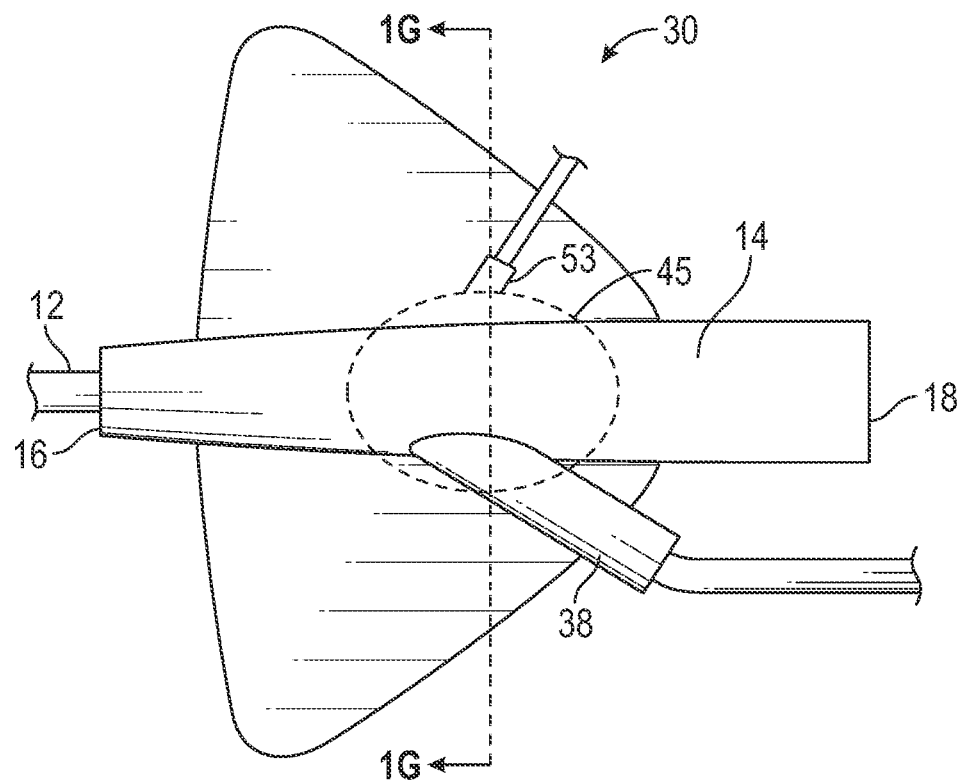
FIG. 1P is an upper perspective view of another catheter assembly, illustrating an example expandable pocket, according to some embodiments.
Figure 1Q:
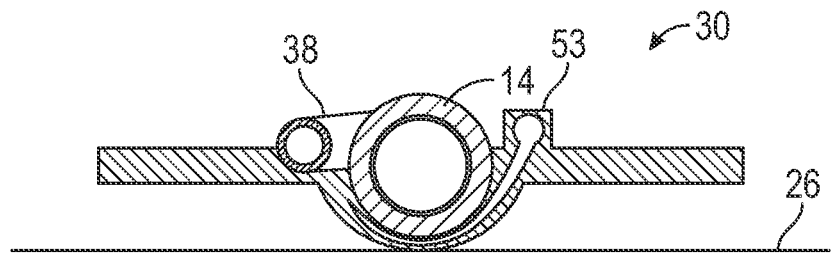
FIG. 1Q is an upper perspective view of the catheter assembly of FIG. 1P, illustrating the expandable pocket prior to filling with liquid or gas, according to some embodiments.
Figure 1R:
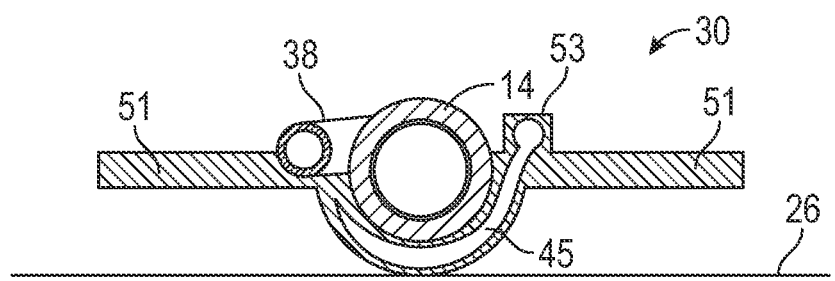
FIG. 1R is an upper perspective view of the catheter assembly of FIG. 1P, illustrating the expandable pocket filled with liquid or gas, according to some embodiments.
Figure 2A:
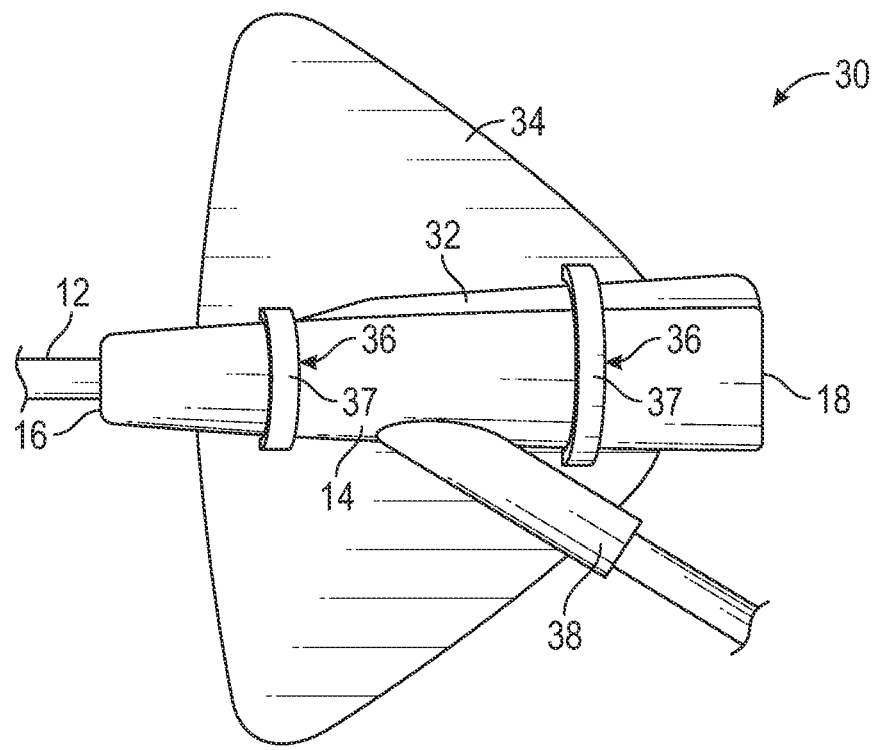
FIG. 2A is an upper perspective view of another catheter assembly, illustrating the catheter assembly in an example first position and an example protrusion, according to some embodiments.
Figure 2B:
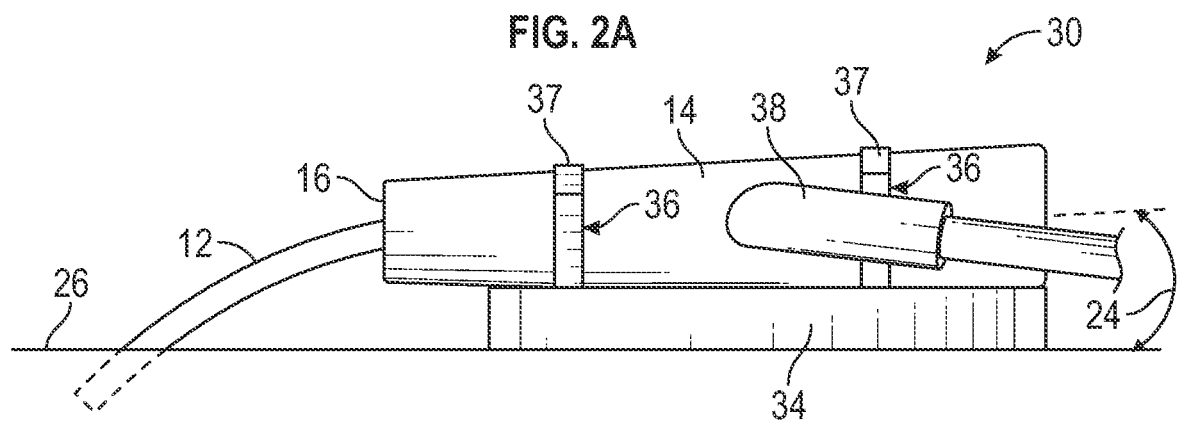
FIG. 2B is a side view of the catheter assembly of FIG. 2A, illustrating the catheter assembly in the first position, according to some embodiments.
Figure 2C:
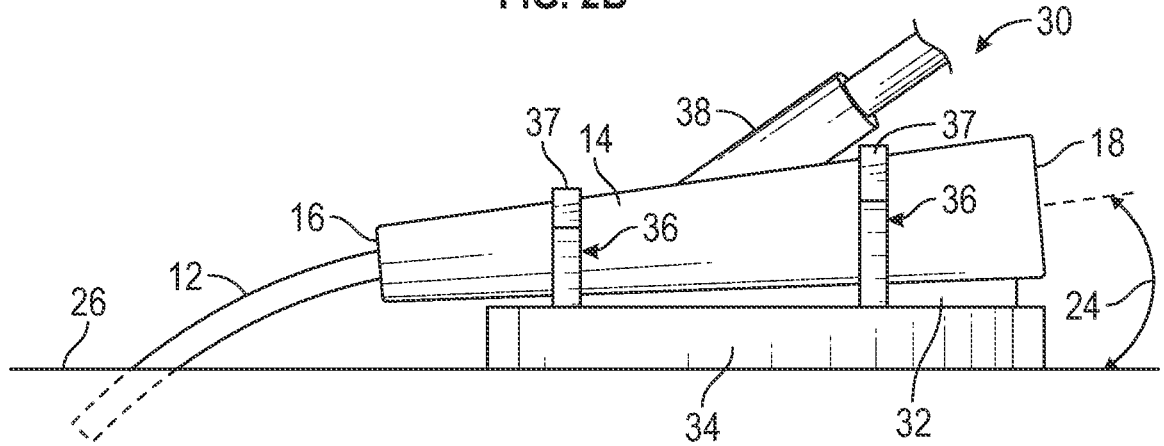
FIG. 2C is a side view of the catheter assembly of FIG. 2A, illustrating the catheter assembly in an example second position, according to some embodiments.

Referring now to FIGS. 1P-1R, in some embodiments, the expandable pocket 45 may be in fluid communication with an infusion port 53 of the catheter adapter 14. In some embodiments, the expandable pocket 45 may be filled in response to fluid or gas flowing into the expandable pocket 45 via the infusion port 53. In some embodiments, the fluid may include saline and/or may be infused into the expandable pocket 45 via a saline flush syringe coupled to an extension set extending from the infusion port 53. Referring now to FIGS. 2A-2C, a catheter assembly 30 is illustrated, according to some embodiments. In some embodiments, the catheter assembly 30 may be similar or identical to the catheter assembly 10 in terms of one or more included features and/or operation. In some embodiments, a protrusion 32 may be coupled to the catheter adapter 14. In some embodiments, the protrusion 32 may include an elongated rib. In these and other embodiments, the protrusion 32 may include a flat or planar surface (illustrated, for example, in FIGS. 2A and 2C), which may stabilize the protrusion against the insertion surface 26. In some embodiments, the protrusion 32 may extend along all or a portion of the catheter adapter 14.

In some embodiments, the protrusion 32 may be configured to rotate. In some embodiments, in response to the protrusion 32 being rotated from a first position to a second position, the angle 24 of the catheter adapter 14 with respect to the insertion surface 26 may be configured to increase. In some embodiments, in response to the protrusion 32 being rotated from the first position to the second position, the catheter adapter 14 may rotate with the protrusion 32. In these and other embodiments, the protrusion 32 may be fixedly attached to the catheter adapter 14 or the catheter adapter 14 and the protrusion 32 may be monolithically formed as a single unit.

In some embodiments, the catheter assembly 30 may include a platform 34. In some embodiments, in response to the protrusion 32 being in the first position, illustrated, for example, in FIGS. 2A-2B, the catheter adapter 14 may rest on the platform 34. In some embodiments, in response to the protrusion 32 being rotated to the second position, illustrated, for example, in FIG. 2B, the protrusion 32 may rest on the platform 34, and the catheter adapter 14 may be spaced apart from the platform 34. In some embodiments, the platform 34 may include securement wings. In some embodiments, the platform 34 may rest on the insertion surface 26.

In some embodiments, the catheter assembly 30 may include one or more straps 36 disposed over the catheter adapter 14 and the protrusion 32. In some embodiments, at least a portion of the straps 36 are elastomeric, which may facilitate lifting of the proximal end 18 of the catheter adapter 14. In some embodiments, the straps 36 may include an elastomeric portion 37. In some embodiments, an upper portion of the straps 36 may be elastomeric, while a lower portion of the straps 36 may be constructed of a more rigid material to provide support to the catheter adapter 14.

In some embodiments, the catheter adapter 14 may include side port 38 disposed between the distal end 16 of the catheter adapter 14 and the proximal end 18 of the catheter adapter 14. In some embodiments, extension tubing may extend from the side port 38 and may be used for infusion into the vasculature and/or blood collection from the vasculature. In some embodiments, the side port 38 may be disposed between two of the straps 36.

Figure 3A:
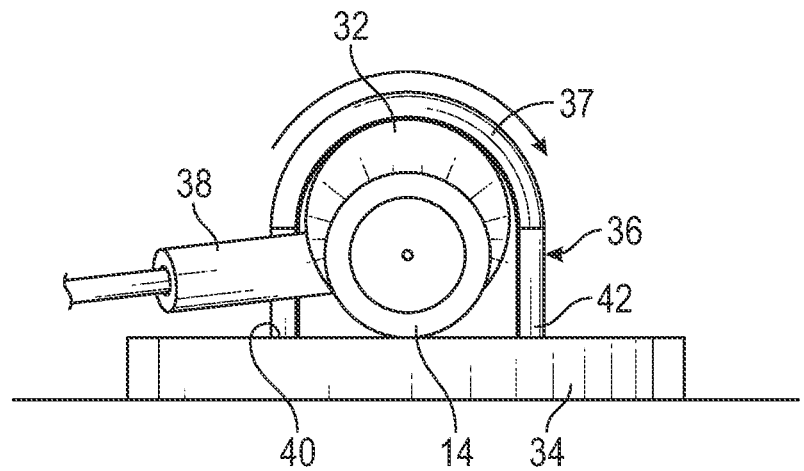
FIG. 3A is a proximal end view of the catheter assembly of FIG. 2A, illustrating the catheter assembly in the first position, according to some embodiments.
Figure 3B:
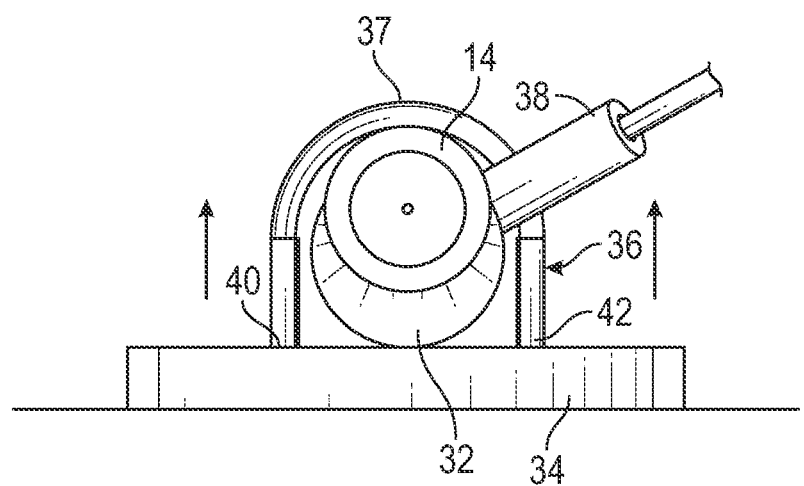
FIG. 3B is a proximal end view of the catheter assembly of FIG. 2A, illustrating the catheter assembly in the second position, according to some embodiments.

Referring now to FIGS. 3A-3B, the catheter assembly 30 is illustrated, according to some embodiments. In some embodiments, the protrusion 32 may be rounded, as illustrated, for example, in FIGS. 3A-3B. In some embodiments, a first end 40 and a second end 42 of one or more of the straps 36 may be coupled to the platform 34. In some embodiments, in response to the protrusion 32 being rotated from a first position, illustrated, for example, in FIG. 3A, to a second position, illustrated, for example, in FIG. 3B, the angle 24 of the catheter adapter 14 with respect to the insertion surface 26 may be configured to increase. In these embodiments, the proximal end 18 of the catheter adapter 14 may be lifted up, which may alter a position of the catheter 12 and improve patency and/or alignment of a fluid path of the catheter assembly 10 with the vasculature.

Referring now to FIGS. 4A-4F, the catheter assembly 30 is illustrated, according to some embodiments. In some embodiments, the catheter assembly 30 may include a collar 44 that rotates with respect to the catheter adapter 14. In some embodiments, the collar 44 may be threaded onto the catheter adapter 14, which may provide secure positioning of the catheter adapter 14. In some embodiments, the collar 44 may be engaged in a slip-fit with the catheter adapter 14 or coupled to the catheter adapter 14 via another suitable means. In some embodiments, the collar 44 may include the protrusion 32. In some embodiments, the collar 44 may be asymmetric. In some embodiments, the catheter adapter 14 may include one or more wings, which may be lifted or lowered with the catheter adapter 14.

Figure 4A:
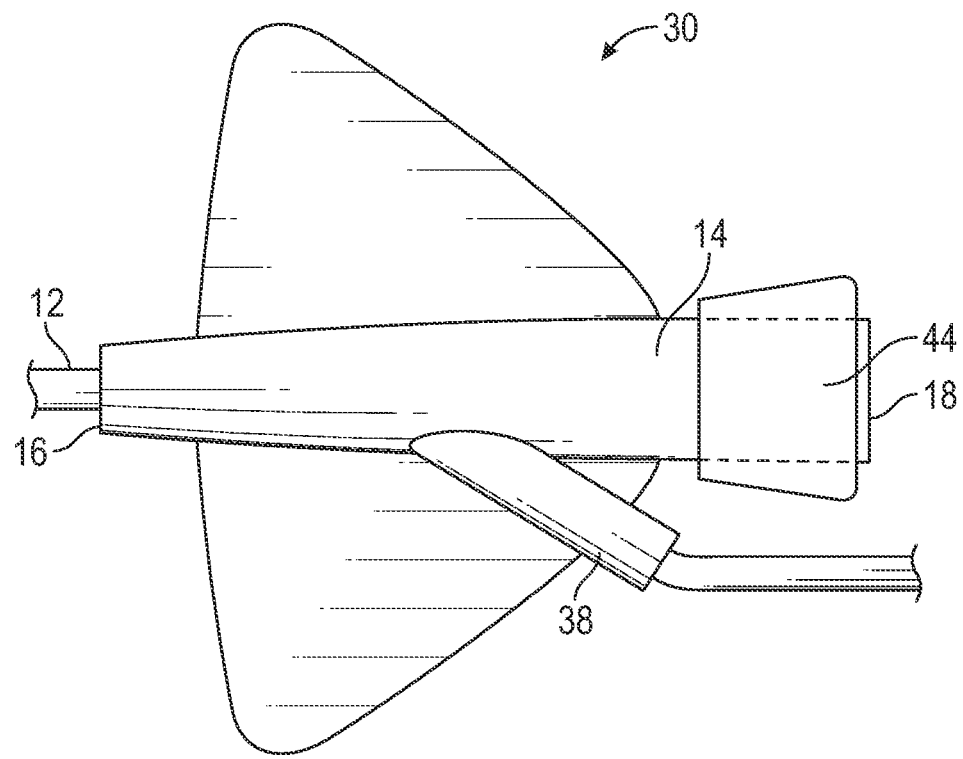
FIG. 4A is an upper perspective view of the catheter assembly of FIG. 2A, illustrating an example collar, according to some embodiments.
Figure 4B:
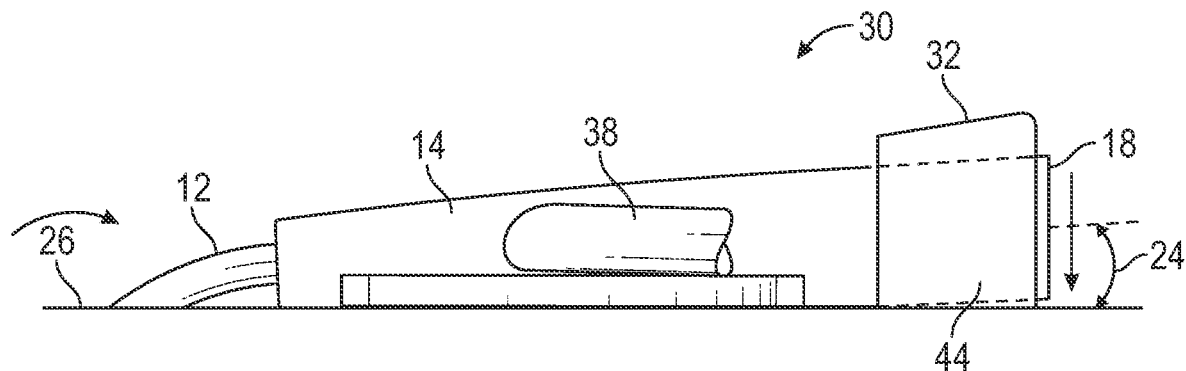
FIG. 4B is a side view of the catheter assembly of FIG. 2A, illustrating the collar in an example first position, according to some embodiments.
Figure 4C:
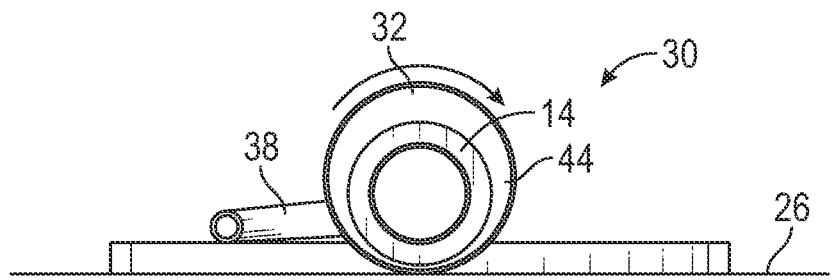
FIG. 4C is a proximal end view of the catheter assembly of FIG. 2A, illustrating the collar in the first position, according to some embodiments.
Figure 4D:
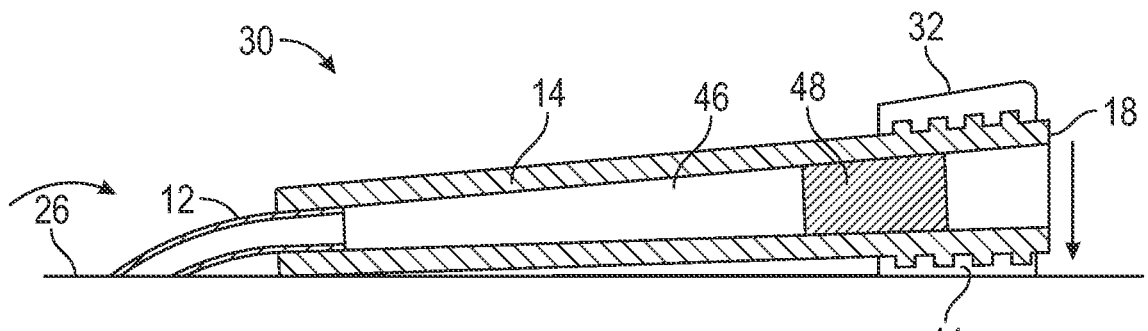
FIG. 4D is a cross-sectional view of the catheter assembly of FIG. 2A, illustrating the collar in the first position, according to some embodiments.
Figure 4E:
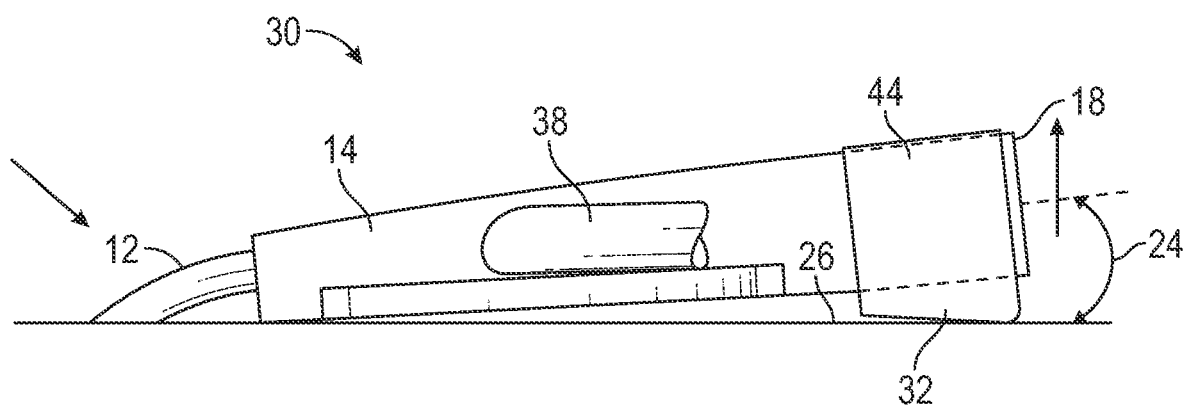
FIG. 4E is a side view of the catheter assembly of FIG. 2A, illustrating the collar in an example second position, according to some embodiments.
Figure 4F:
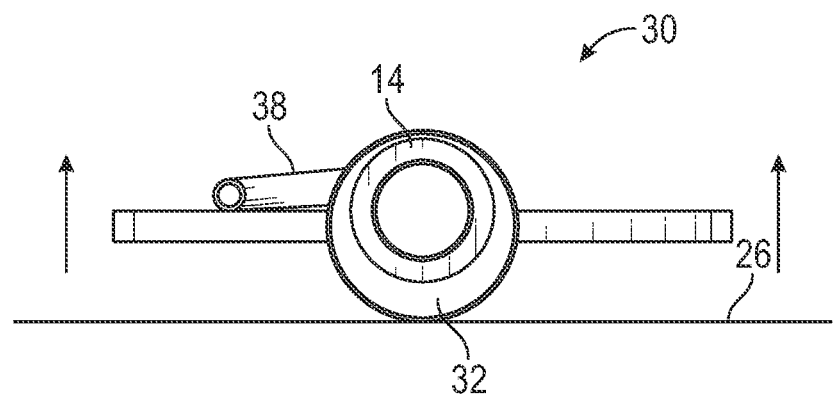
FIG. 4F is a proximal end view of the catheter assembly of FIG. 2A, illustrating the collar in the second position, according to some embodiments.

In some embodiments, in response to the protrusion 32 being rotated from a first position, illustrated, for example, in FIGS. 4A-4D, to a second position, illustrated, for example, in FIGS. 4E-4F, the angle 24 of the catheter adapter 14 with respect to the insertion surface 26 may be configured to increase. In these embodiments, the proximal end 18 of the catheter adapter 14 may be lifted up, which may alter a position of the catheter 12 and improve patency and/or alignment of a fluid path of the catheter assembly 30 with the vasculature. FIG. 4D illustrates the lumen 46 of the catheter adapter 14, which may include a septum 48 to prevent blood leakage through the proximal end 18.

Figure 5A:
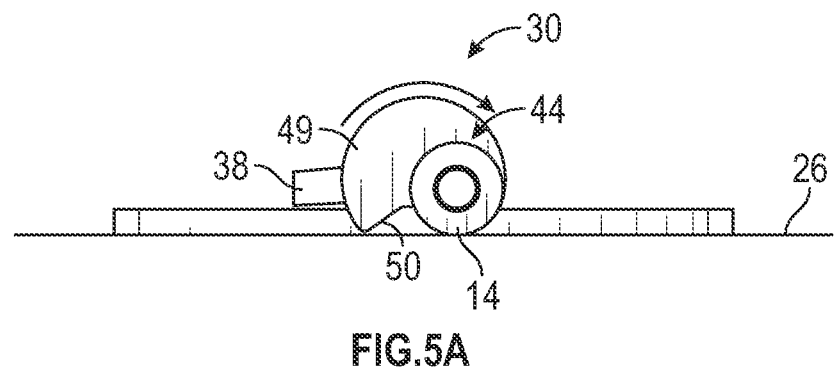
FIG. 5A is a proximal end view of the catheter assembly of FIG. 2A, illustrating another example collar in an example first position, according to some embodiments.
Figure 5B:
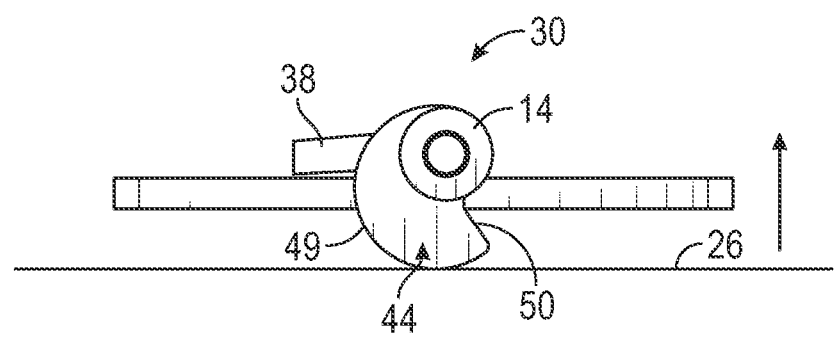
FIG. 5B is a proximal end view of the catheter assembly of FIG. 2A, illustrating the other example collar in an example second position, according to some embodiments.

Referring now to FIG. 5A-5B, the catheter assembly 30 is illustrated, according to some embodiments. In some embodiments, the collar 44 may include various shapes, such as a smooth curve 49 proximate a radial surface 50, which may be generally perpendicular to the smooth curve 49 and may facilitate rotation by the user. In some embodiments, the collar 84 may entirely surround the catheter adapter 14. In some embodiments, in response to the protrusion 32 being rotated from the first position, illustrated, for example, in FIG. 5A, to the second position, illustrated, for example, in FIG. 5B, an angle (see, for example, the angle 24 of FIGS. 1A-1B of FIGS. 2B-2C) of the catheter adapter 14 with respect to the insertion surface 26 may be configured to increase.

Figure 6A:
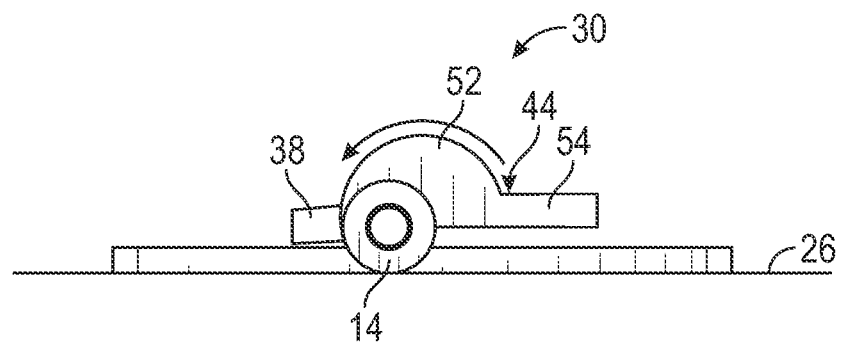
FIG. 6A is a proximal end view of the catheter assembly of FIG. 2A, illustrating another example collar in an example first position, according to some embodiments.
Figure 6B:
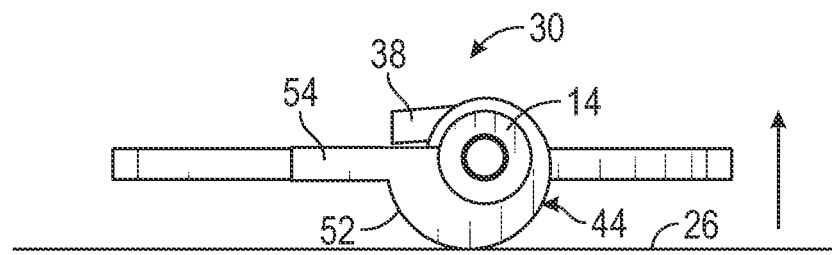
FIG. 6B is a proximal end view of the catheter assembly of FIG. 2A, illustrating the other collar of FIG. 6A in an example second position, according to some embodiments.

Referring now to FIG. 6A-6B, the catheter assembly 30 is illustrated, according to some embodiments. In some embodiments, the collar 44 may include various shapes, such as a smooth curve 52 proximate a tab 54 to facilitate gripping and rotation by the user. In some embodiments, in response to the protrusion 32 being rotated from the first position, illustrated, for example, in FIG. 5A, to the second position, illustrated, for example, in FIG. 5B, an angle of the catheter adapter 14 with respect to the insertion surface 26 may be configured to increase.

Figure 7A:
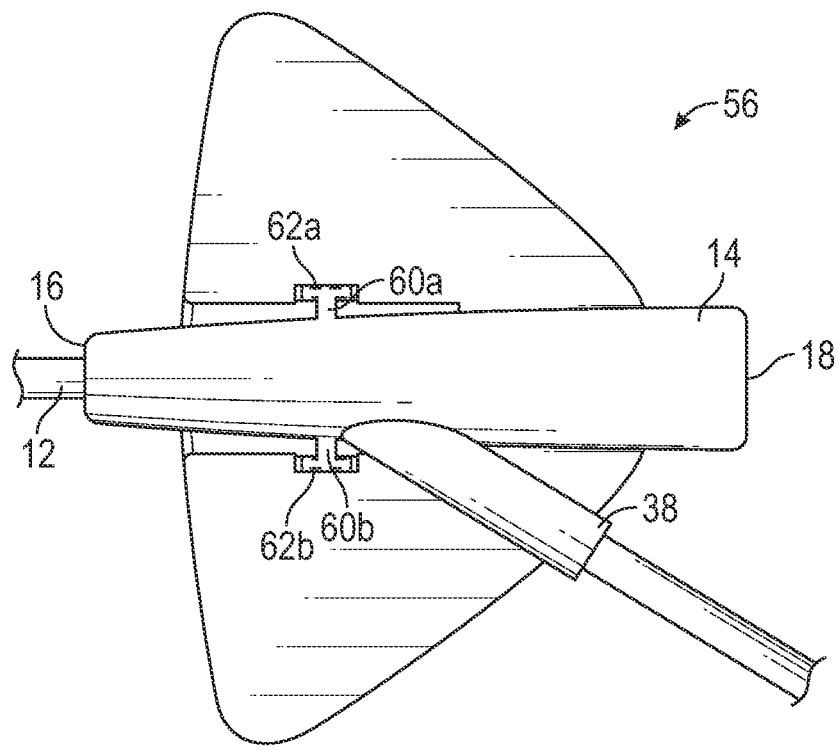
FIG. 7A is an upper perspective view of another catheter assembly, according to some embodiments.
Figure 7B:
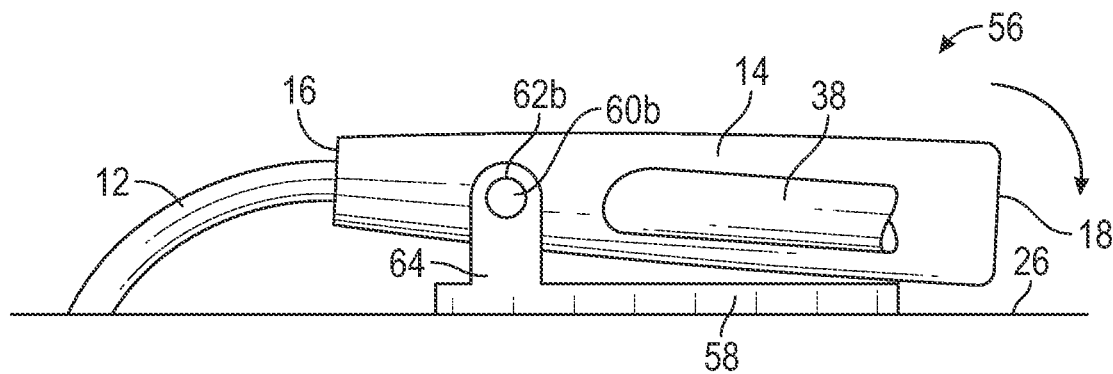
FIG. 7B is a side view of the catheter assembly of FIG. 7A, illustrating the catheter assembly in an example first position, according to some embodiments.
Figure 7C:
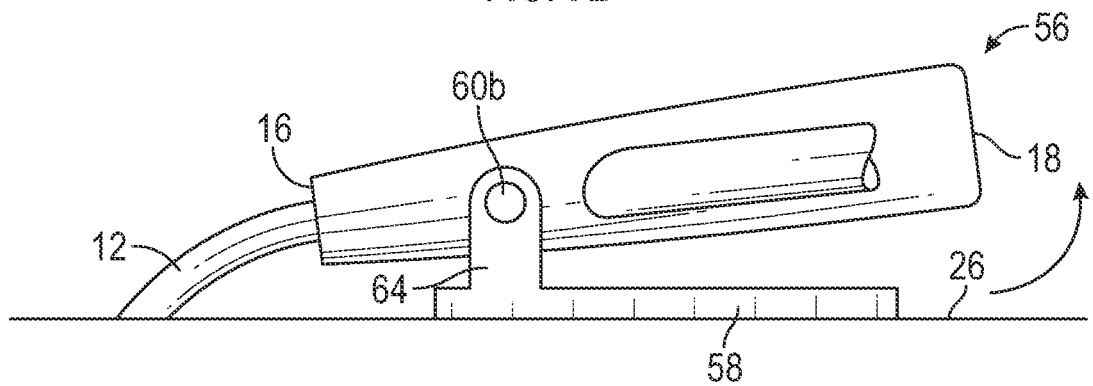
FIG. 7C is a side view of the catheter assembly of FIG. 7A, illustrating the catheter assembly in an example second position, according to some embodiments.

Referring now to FIGS. 7A-7C, a catheter assembly 56 is illustrated, according to some embodiments. In some embodiments, the catheter assembly 56 may be similar or identical to the catheter assembly 10 and/or the catheter assembly 30 in terms of one or more included features and/or operation.

In some embodiments, the catheter assembly 56 may include a platform 58 that is pivotally coupled to the catheter adapter 14. In some embodiments, the catheter adapter 14 may be configured to pivot between a first position, illustrated, for example, in FIGS. 7A-7B, and a second position, illustrated, for example, in FIG. 7C. In some embodiments, in response to the catheter adapter 14 pivoting from the first position to the second position, an angle of the catheter adapter 14 with respect to the insertion surface is configured to increase, and the proximal end 18 of the catheter adapter 14 may be lifted. In some embodiments, a first shaft 60a and a second shaft 60b may extend from opposite sides of the catheter adapter 14 and may be configured to rotate within grooves 62a, 62b, respectively, to move the catheter adapter 14 between the first position and the second position. In some embodiments, the grooves 62a, 62b may be disposed within walls 64 extending upwardly from the platform 58.

Figure 8A:
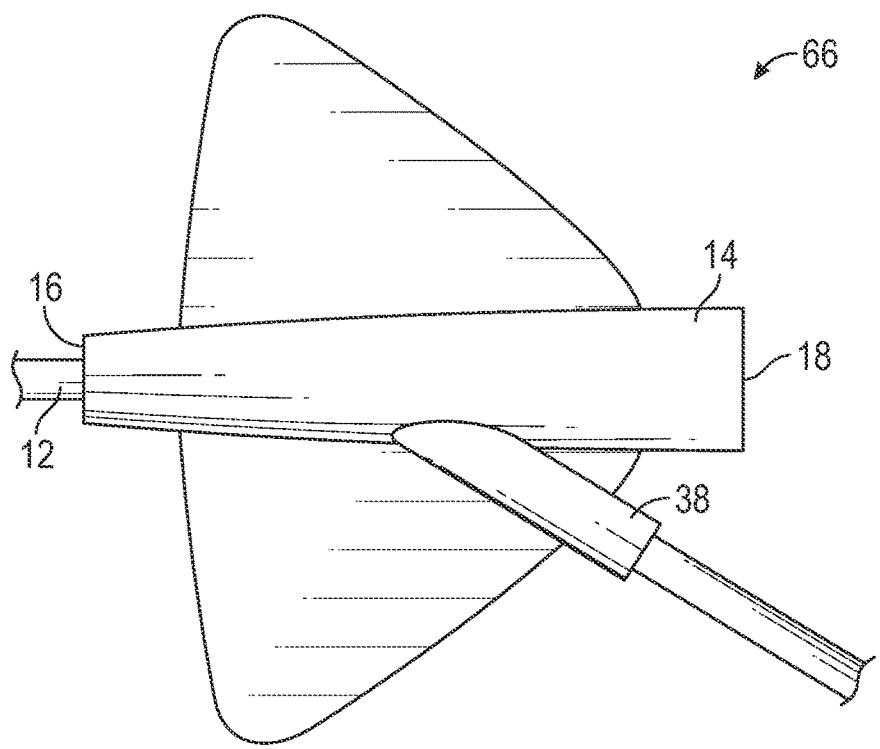
FIG. 8A is an upper perspective view of another catheter assembly, according to some embodiments.
Figure 8B:
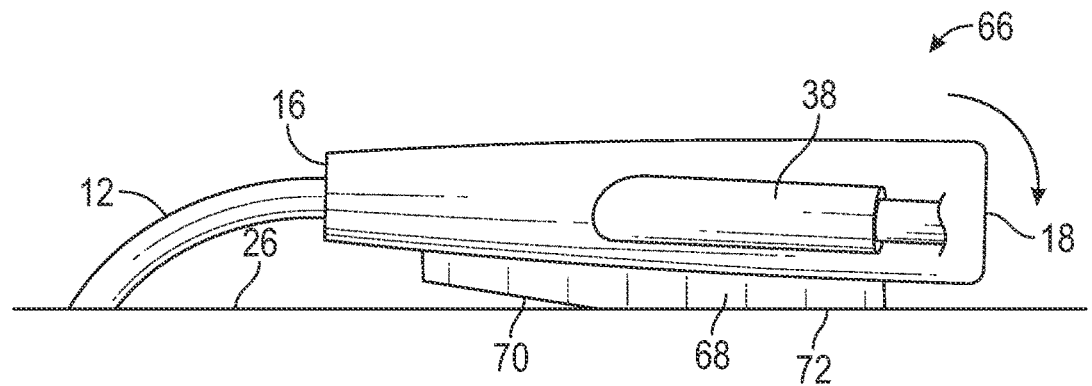
FIG. 8B is a side view of the catheter assembly of FIG. 8A, illustrating the catheter assembly in an example first position, according to some embodiments.
Figure 8C:
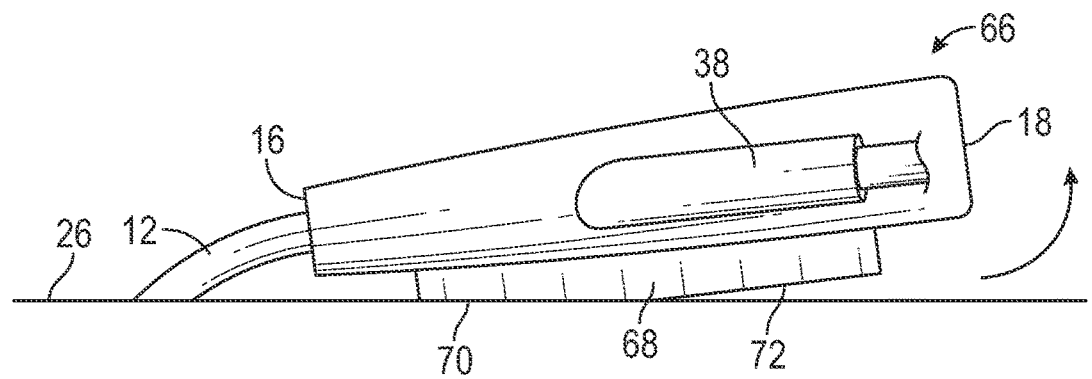
FIG. 8C is a side view of the catheter assembly of FIG. 8A, illustrating the catheter assembly in an example second position, according to some embodiments.

Referring now to FIGS. 8A-8C, a catheter assembly 66 is illustrated, according to some embodiments. In some embodiments, the catheter assembly 66 may be similar or identical to one or more of the following: the catheter assembly 10, the catheter assembly 30, and the catheter assembly 56, in terms of one or more included features and/or operation.

In some embodiments, the catheter assembly 66 may include a platform 68 coupled to the catheter adapter 14. In some embodiments, the platform 68 may include a first planar surface 70 and a second planar surface 72 proximate the first planar surface 70. In some embodiments, the first planar surface 70 may be angled with respect to the second planar surface 72. In some embodiments, the catheter adapter 14 may be configured to rock between a first position, illustrated, for example, in FIGS. 8A-8B, to a second position, illustrated, for example, in FIG. 8C. In some embodiments, the first planar surface 70 may contact the insertion surface 26 in the first position, and the second planar surface 72 may be spaced apart from the insertion surface 26. In some embodiments, the second planar surface 72 may contact the insertion surface 26 in the second position, and the first planar surface 70 may be spaced apart from the insertion surface 26.

In some embodiments, in response to the user rocking the catheter adapter 14 from the first position to the second position, the angle 24 of the catheter adapter 14 with respect to the insertion surface may be configured to increase, and the proximal end 18 of the catheter adapter 14 is lifted up, changing a position of the catheter 12 and improving patency and alignment.

Figure 9A:
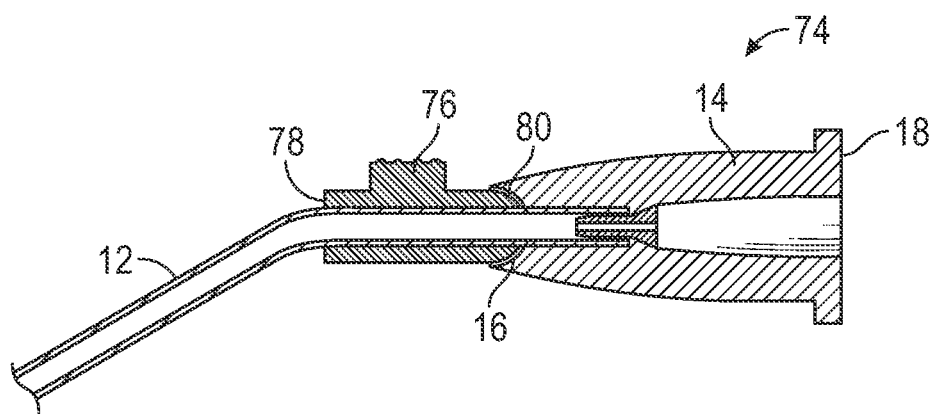
FIG. 9A is a cross-sectional view of another example catheter assembly, illustrating an example catheter adjuster in an example first position, according to some embodiments.
Figure 9B:
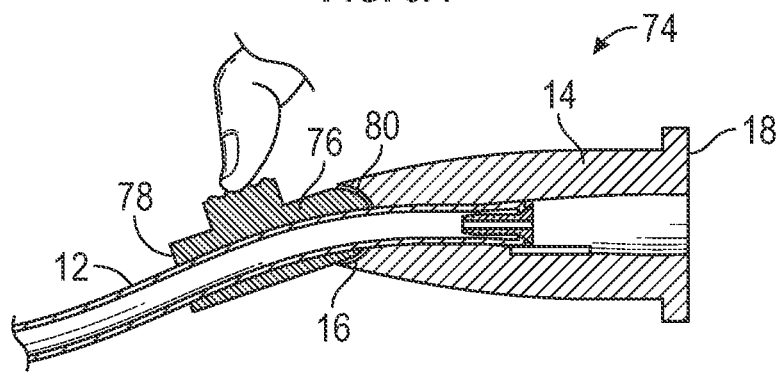
FIG. 9B is a cross-sectional view of the catheter assembly of FIG. 9A, illustrating the catheter adjuster in an example second position, according to some embodiments.
Figure 9C:
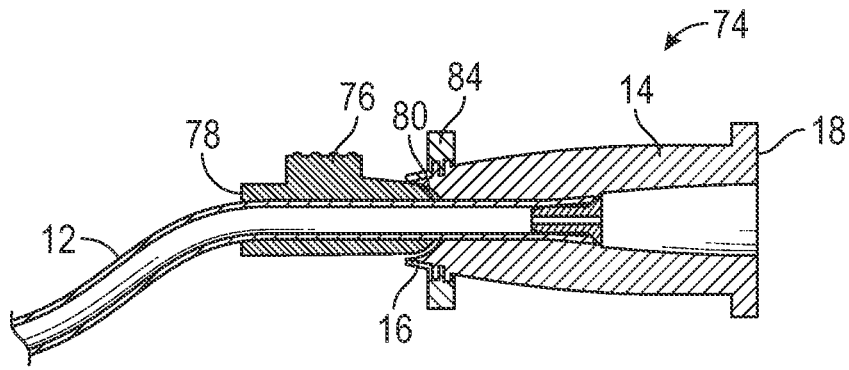
FIG. 9C is a cross-sectional view of the catheter assembly of FIG. 9A, illustrating the catheter adjuster in a locked position, according to some embodiments.

Referring now to FIGS. 9A-9C, a catheter assembly 74 is illustrated, according to some embodiments. In some embodiments, the catheter assembly 74 may be similar or identical to one or more of the following: the catheter assembly 10, the catheter assembly 30, the catheter assembly 56, and the catheter assembly 66, in terms of one or more included features and/or operation.

In some embodiments, the catheter assembly 74 may include a catheter adjuster 76, which may include a distal end 78, a proximal end 80, and the catheter 12 extending there through. In some embodiments, the catheter adjuster 76 may be coupled to the distal end 16 of the catheter adapter 14 at a ball joint 82, a hinge, or another suitable mechanism.

As illustrated, for example, in FIGS. 9A-9C, the distal end 16 of the catheter adapter 14 may include a socket and the proximal end 80 of the catheter adjuster 76 may include a ball or rounded portion configured to rotate within the socket. Alternatively, in some embodiments, the distal end 16 of the catheter adapter 14 may include the ball or rounded portion and the proximal end 80 of the catheter adjuster 76 may include the socket.

In some embodiments, the catheter adjuster 76 may move from a first position, illustrated, for example, in FIG. 9A, to a second position, illustrated, for example, in FIG. 9B, via the ball joint 82 or the hinge. In some embodiments, in response to the catheter adjuster 76 moving from the first position to the second position, an angle of the catheter 12 with respect to the insertion surface 26 may be configured to increase.

As illustrated, for example, in FIG. 9C, the catheter assembly 74 may include a collar 84 disposed around the distal end 16 of the catheter adapter 14. In some embodiments, the collar 84 may be configured to lock the ball joint 82 in the first position or the second position. In some embodiments, the collar 84 may include threads corresponding to other threads of an outer surface of the distal end 16 of the catheter adapter 14. In some embodiments, the collar 84 may partially or entirely surround the catheter adapter 14.

Figure 9D:
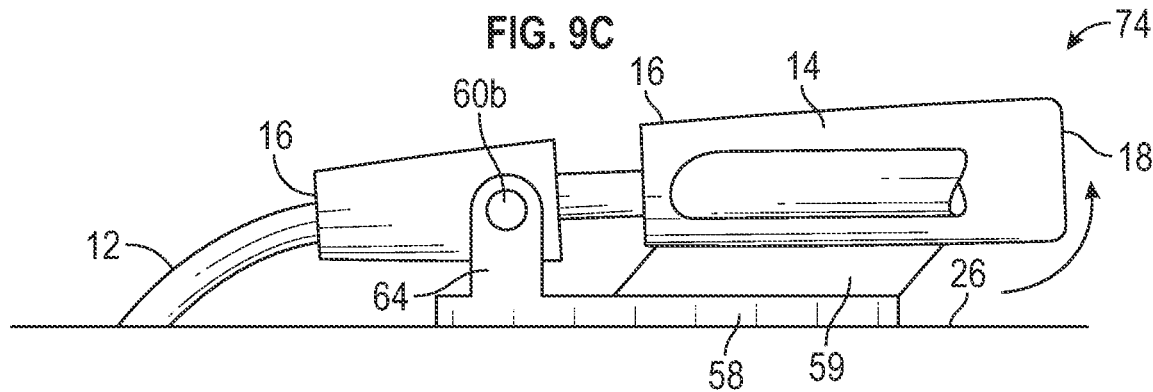
FIG. 9D is a side view of the catheter assembly of FIG. 9A, illustrating an example platform pivotally coupled to the catheter adapter, according to some embodiments.

Referring now to FIG. 9D, in some embodiments, the catheter assembly 74 may include the platform 58, which may be pivotally coupled to the catheter adjuster 76 through which the catheter 12 extends. In some embodiments, the platform 58 may include a protrusion 59 upon which the catheter adapter 14 may rest.

In some embodiments, the catheter adjuster 76 may be configured to pivot between the first position and the second position via the hinge. In some embodiments, in response to the catheter adjuster 76 pivoting from the first position to the second position, the catheter 12 may bend and an angle of a distal end of the catheter 12 with respect to the insertion surface is configured to increase. In some embodiments, the proximal end 18 of the catheter adapter 14 may remain still on the protrusion 59 or the platform 58 in response to the catheter adjuster 76 pivoting from the first position to the second position. In some embodiments, the first shaft 60a and the second shaft 60b may be fixed to the catheter adjuster 76. In some embodiments, the first shaft 60a and the second shaft 60b may extend from opposite sides of the catheter adapter 14 and may be configured to rotate within grooves 62a, 62b (see, for example, FIG. 7A), respectively, to move the catheter adjuster 76 and the catheter 12 between the first position and the second position. In some embodiments, the grooves 62a, 62b may be disposed within walls 64 extending upwardly from the platform 58.

Figure 10A:
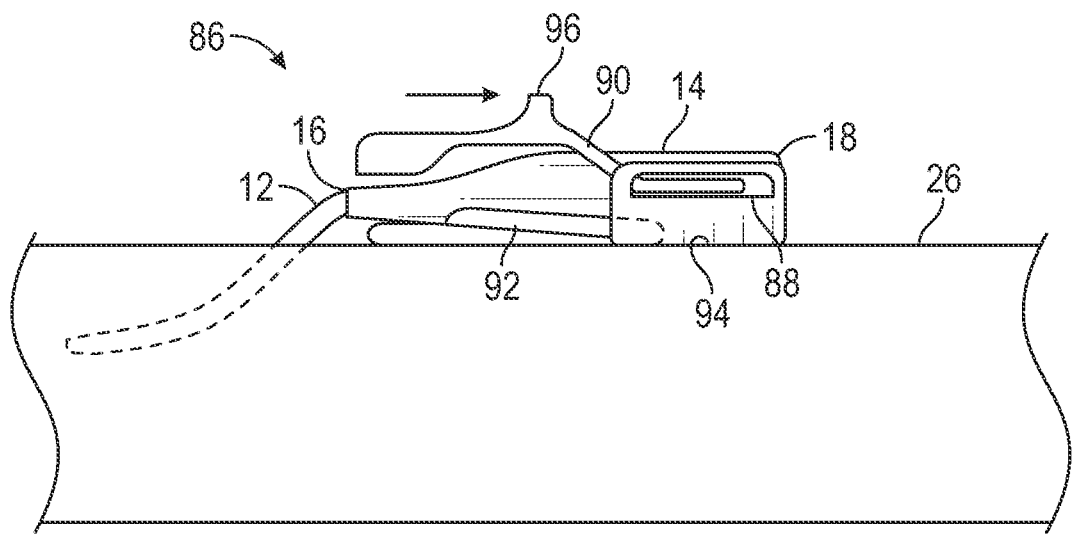
FIG. 10A is a side view of another catheter assembly, illustrating an example slider in an example distal position, according to some embodiments.
Figure 10B:
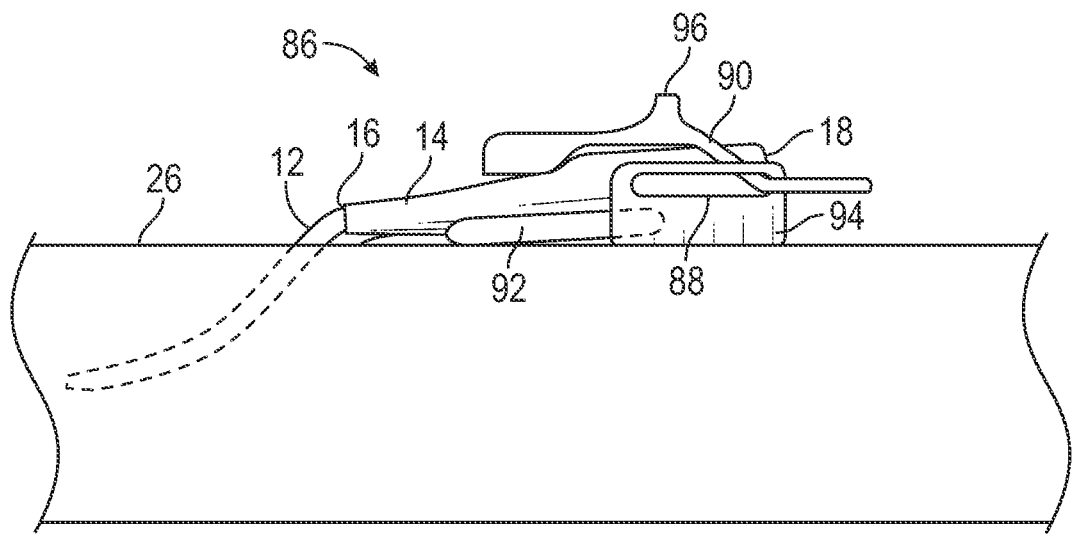
FIG. 10B is a side view of the catheter assembly of FIG. 10A, illustrating the slider in an example proximal position, according to some embodiments.

Referring now to FIGS. 10A-10B, a catheter assembly 86 is illustrated, according to some embodiments. In some embodiments, the catheter assembly 86 may be similar or identical to one or more of the following: the catheter assembly 10, the catheter assembly 30, the catheter assembly 56, the catheter assembly 66, and the catheter assembly 74, in terms of one or more included features and/or operation.

In some embodiments, the catheter adapter 14 may include a slot 88. In some embodiments, the catheter assembly 86 may include a slider 90 extending through the slot 88 and configured to move within the slot 88 between a proximal position, illustrated, for example, in FIG. 10B, and a distal position, illustrated, for example, in FIG. 10A. In some embodiments, in response to the slider 90 moving from the proximal position to the distal position, the slider may push on the distal end 16 of the catheter adapter 14 to increase the angle of the catheter adapter 14 with respect to the insertion surface 26.

In some embodiments, the catheter adapter 14 may include a wing 92 and a wall 94 extending generally perpendicular to the wing 92. In some embodiments, the slot 88 is disposed within the wall 94. In some embodiments, the slider 90 may be arched. In some embodiments, the slider 90 may include a protrusion or push tab 96 disposed on a top of the slider 90 and configured for gripping by the user. In some embodiments, the catheter adapter 14 may not include the slide 90, the wall 94, and the slot 88, which may be incorporated into a stabilization device or dressing coupled to the catheter adapter 14 or near the catheter adapter 14.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A catheter assembly, comprising:
   a catheter adapter, comprising a distal end, a proximal end, and a lumen extending through the distal end and the proximal end;
   a catheter secured within the catheter adapter and extending from the distal end of the catheter adapter;
   an expandable support coupled to the catheter adapter, wherein the expandable support has an adjustable height configured to adjust an angle of the catheter adapter with respect to skin of the patient, wherein the adjustable height of the expandable support is configured to increase from a diminished position to an expanded position in response to an infusion of liquid or air into the expandable support.

2. A catheter assembly, comprising:
a catheter adapter, comprising a distal end, a proximal end, and a lumen extending through the distal end and the proximal end;
a catheter secured within the catheter adapter and extending from the distal end of the catheter adapter; and
a protrusion coupled to the catheter adapter, wherein the protrusion is configured to rotate about a central longitudinal axis of the catheter adapter, wherein in response to the protrusion being rotated from a first position to a second position, an angle of the catheter adapter with respect to an insertion surface is configured to increase.

3. The catheter assembly of claim 2, wherein in response to the protrusion being rotated from the first position to the second position, the catheter adapter rotates with the protrusion.

4. The catheter assembly of claim 3, further comprising a platform, wherein in response to the protrusion being in the first position, the catheter adapter rests on the platform, wherein in response to the protrusion being rotated to the second position, the protrusion rests on the platform and the catheter adapter is spaced apart from the platform.

5. The catheter assembly of claim 4, wherein the catheter adapter and the protrusion are monolithically formed as a single unit.

6. The catheter assembly of claim 2, further comprising a strap disposed over the catheter adapter and the protrusion, wherein a first end and a second end of the strap are coupled to the platform, wherein at least a portion of the strap is elastomeric.

7. The catheter assembly of claim 6, further comprising another strap disposed over the catheter adapter and the protrusion, wherein a first end and a second end of the other strap are coupled to the platform, wherein at least a portion of the other strap is elastomeric.

8. The catheter assembly of claim 7, wherein the catheter adapter further comprises a side port disposed between the distal end of the catheter adapter and the proximal end of the catheter adapter, wherein the side port is disposed between the strap and the other strap.

9. The catheter assembly of claim 2, further comprising a collar that rotates with respect to the catheter adapter, wherein the collar comprises the protrusion, wherein the collar is asymmetric.

10. A catheter assembly, comprising:
a catheter adapter, comprising a distal end, a proximal end, and a lumen extending through the distal end and the proximal end;
a catheter secured within the catheter adapter and extending from the distal end of the catheter adapter; and
a platform coupled to the catheter adapter, wherein the platform comprises a first planar surface and a second planar surface proximate the first planar surface, wherein the first planar surface is angled with respect to the second planar surface, wherein the first and second planar surfaces are configured to contact an insertion surface of a patient, wherein the catheter adapter is configured to rock in a direction along a central longitudinal axis of the catheter adapter between (i) a first position in which the first planar surface contacts the insertion surface, to (ii) a second position in which the second planar surface contacts the insertion surface, wherein in response to the catheter adapter rocking from the first position to the second position, the angle of the catheter adapter with respect to the insertion surface is configured to increase.

11. A catheter assembly, comprising:
a catheter adapter, comprising a distal end, a proximal end, and a lumen extending through the distal end and the proximal end; and
a catheter secured within the catheter adapter and extending from the distal end of the catheter adapter,
wherein the catheter adapter comprises a slot, further comprising a slider extending through the slot and configured to move between a proximal position and a distal position, wherein in response to the slider moving from the proximal position to the distal position, the slider pushes on the distal end of the catheter adapter to increase the angle of the catheter adapter with respect to an insertion surface.

12. The catheter assembly of claim 11, wherein the catheter adapter comprises a wing and a wall extending generally perpendicular to the wing, wherein the slot is disposed within the wall.

13. The catheter assembly of claim 11, wherein the slider is arched.

14. The catheter assembly of claim 11, wherein the slider comprises a push tab on a top of the slider.

15. A catheter assembly, comprising:
a catheter adapter, comprising a concave distal end, a proximal end, and a lumen extending through the distal end and the proximal end;
a catheter secured within the catheter adapter and extending from the distal end of the catheter adapter;
a catheter adjuster comprising a distal end and a convex proximal end, wherein the proximal end of the catheter adjuster is coupled to the distal end of the catheter adapter to form a ball joint, wherein the catheter extends through the catheter adjuster and the ball joint, wherein in response to the catheter adjuster moving from a first position to a second position via the ball joint, an angle of the catheter with respect to an insertion surface is configured to increase; and
a collar threadably disposed around the distal end of the catheter adapter, wherein the collar is configured to lock the ball joint in the first position or the second position.

* * * * *